United States Patent [19]

Hirai et al.

[11] 4,341,704
[45] Jul. 27, 1982

[54] 4,1-BENZOXAZEPINES AND THIA ANALOGS THEREOF

[75] Inventors: Kentaro Hirai, Kyoto; Shigeru Matsutani, Sakai; Teruyuki Ishiba, Takatsuki; Itsuo Makino, Kobe, all of Japan

[73] Assignee: Shionogi & Co., Ltd., Osaka, Japan

[21] Appl. No.: 276,632

[22] Filed: Jun. 23, 1981

Related U.S. Application Data

[62] Division of Ser. No. 91,814, Nov. 6, 1979, Pat. No. 4,297,280.

[30] Foreign Application Priority Data

Nov. 27, 1978 [JP] Japan .................................. 53-146949

[51] Int. Cl.³ .......................................... C07D 513/04
[52] U.S. Cl. .................................................. 260/243.3
[58] Field of Search ...................... 260/243.3; 544/184

[56] References Cited

U.S. PATENT DOCUMENTS 3,818,003  6/1974  Szmuszkovicz ................ 544/184
3,933,816  1/1976  Szmuszkovicz ................ 544/184
4,180,668 12/1979  Hester ........................ 260/243.3

*Primary Examiner*—John M. Ford
*Attorney, Agent, or Firm*—Wenderoth, Lind & Ponack

[57] ABSTRACT

4,1-Benzoxazepines and thia analogs thereof of the formula:

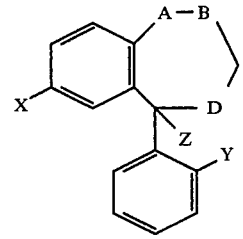

(wherein —A—B— is the following group:

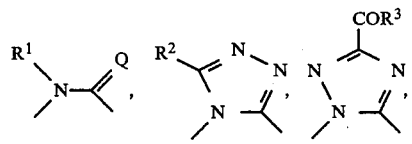

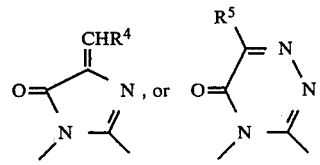

(wherein
$R^1$ is hydrogen, $C_1$ to $C_3$ alkyl, or $C_7$ to $C_9$ aralkyl;
$R^2$ is $C_1$ to $C_3$ alkyl or $C_1$ to $C_3$ α-aminoalkyl;
$R^3$ is $C_2$ to $C_6$ dialkylamino;
$R^4$ is $C_2$ to $C_6$ dialkylamino or $C_5$ to $C_7$ alkylpiperazino;
$R^5$ is $C_1$ to $C_3$ alkyl; and
Q is oxygen or sulfur);
D is oxygen or sulfur;
X is halogen or nitro;
Y is hydrogen or halogen; and
Z is hydrogen, $C_1$ to $C_3$ alkoxy, or $C_3$ to $C_9$ dialkylaminoalkoxy;
with the proviso that when —A—B— is

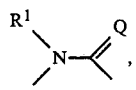

Z is not hydrogen.)
useful as novel central nervous system drugs are prepared by various synthetic routes.

3 Claims, No Drawings

4,1-BENZOXAZEPINES AND THIA ANALOGS THEREOF

This application is a division of Ser. No. 91,814, filed Nov. 6, 1979 now U.S. Pat. No. 4,297,280.

I. BACKGROUND OF THE INVENTION

Various 1,4-benzodiazepine compounds including nitrazepam, diazepam, medazepam, estazolam, and triazolam have been practically used as hypnotics, minor tranquilizers or psychotropic drugs. Recently, the mental disorders show a tendency to rapidly increase together with growth of the complexities in human society. As a result of intensive researches for central nervous system drugs which are more effective and broadly applicable to mental disorders, the present inventors have found that 4,1-benzoxazepines and 4,1-benzothiazepines have excellent central nervous system actions. This invention is based on this finding. The compounds having 1,4-benzodiazepine structure are well-known, and some compounds having 4,1-benzoxazepine or 4,1-benzothiazepine structure are described in German Pat. No. 1,545,639, U.S. Pat. No. 3,346,638, Farmaco. Ed. Sci., 18, 815 (1963) and Ann. Chem., 1978, 1241. But the compounds of this invention shown hereinafter are novel.

II. SUMMARY OF THE INVENTION

This invention relates to novel 4,1-benzoxazepines and 4,1-benzothiazepines having excellent central nervous system actions.

The compounds of this invention are represented by the formula:

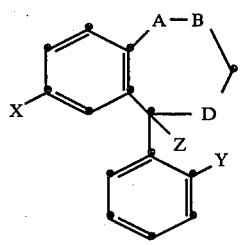

[I]

(wherein —A—B— is the following group:

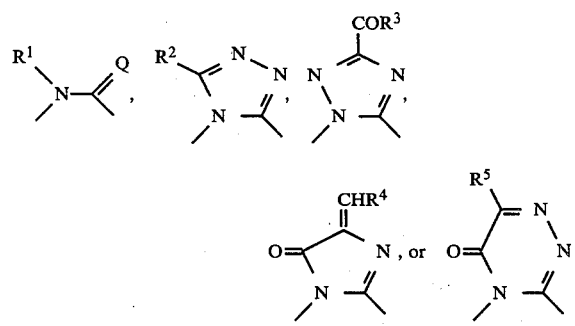

(wherein
$R^1$ is hydrogen, $C_1$ to $C_3$ alkyl, or $C_7$ to $C_9$ aralkyl;
$R^2$ is $C_1$ to $C_3$ alkyl or $C_1$ to $C_3$ α-aminoalkyl;
$R^3$ is $C_2$ to $C_6$ dialkylamino;
$R^4$ is $C_2$ to $C_6$ dialkylamino or $C_5$ to $C_7$ alkylpiperazino;
$R^5$ is $C_1$ to $C_3$ alkyl; and
Q is oxygen or sulfur);
D is oxygen or sulfur;
X is halogen or nitro;
Y is hydrogen or halogen; and
Z is hydrogen, $C_1$ to $C_3$ alkoxy, or $C_3$ to $C_9$ dialkylaminoalkoxy;
with the proviso that when —A—B— is

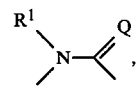

Z is not hydrogen.)

III. DETAILED DESCRIPTION OF THE INVENTION

Representatives of Compounds [I] are:
(1) 1-methyl-6-(2-chlorophenyl)-8-chloro-4H,6H-(1,2,4)triazolo[4,3-a][4,1]benzoxazepine;
(2) 1-methyl-6-(2-chlorophenyl)-8-chloro-4H,6H-(1,2,4)triazolo[4,3-a][4,1]benzothiazepine;
(3) 1-oxo-2-(N,N-dimethylamino)methylidene-6-(2-chlorophenyl)-8-chloro-1,2-dihydro-4H,6H-imidazol[1,2-a][4,1]benzoxazepine;
(4) 1-oxo-2-methyl-7-(2-chlorophenyl)-9-chloro-1,12-dihydro-5H,7H-(1,2,4)triazino[4,3-a][4,1]benzoxazepine;
(5) 2-(N,N-dimethylcarbamoyl)-6-ethoxy-6-(2-chlorophenyl)-8-chloro-4H,6H-(1,2,4)triazolo[2,3-a][4,1]benzoxazepine.

The compounds [I] of this invention also include the acid addition salts, particularly non-toxic pharmaceutically acceptable salts, for example, salts with inorganic acids such as hydrochloric acid, hydrobromic acid, hydroiodic acid, sulfuric acid, carbonic acid, etc., and salts with organic acids such as acetic acid, oxalic acid, succinic acid, phthalic acid, malic acid, tartaric acid, maleic acid, citric acid, mandelic acid, ascorbic acid, etc.

In the aforementioned definition, halogen means fluorine, chlorine, bromine, and the like. $C_1$ to $C_3$ Alkyl includes methyl, ethyl, propyl, isopropyl, etc. $C_1$ to $C_3$ Alkoxy includes methoxy, ethoxy, propoxy, isopropoxy, etc. $C_7$ to $C_9$ Aralkyl includes benzyl, phenethyl, phenylpropyl, etc. $C_2$ to $C_6$ Dialkylamino and $C_5$ to $C_7$ alkylpiperazino mean amino and piperazino substituted by the above alkyl or alkyls, respectively. $C_3$ to $C_9$ Dialkylaminoalkoxy means the above $C_1$ to $C_3$ alkoxy substituted by the above $C_2$ to $C_6$ dialkylamino. $C_1$ to $C_3$ α-Aminoalkyl means the above alkyls of which hydrogen at the α-position is substituted by amino.

This invention also provides for the preparation of the compounds [I]. The preparation varies with the species of substituents. The preparation of the compounds [I] comprises
(1) subjecting a compound of the formula:

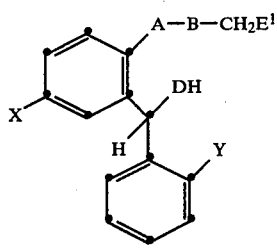

(wherein
 X, Y, —A—B—, and D each is the same as mentioned above; and
 $E^1$ is halogen)
to dehydrohalogenation and, if required, to reaction with phosphorus pentasulfide and/or to alkylation in an inert solvent;

(2) subjecting a compound of the formula:

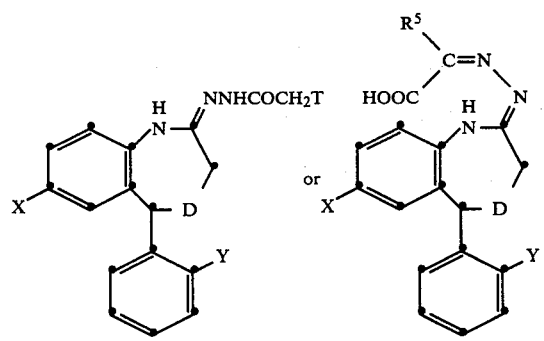

(wherein
 X, Y, $R^5$, and D are the same as mentioned above; and
 T is hydrogen or alkyl)
to cyclization and, if required, to reaction with N-bromosuccinimide and sodium azide, followed by reduction in an inert solvent;

(3) subjecting a compound of the formula:

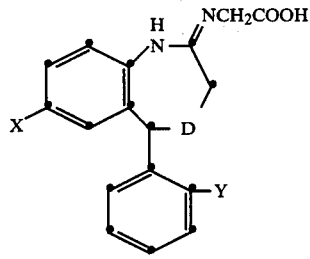

(wherein X, Y, and D are the same as mentioned above)
to cyclization and, if required, to dialkylaminomethylidene formation and alkylpiperazinomethylidene formation in an inert solvent; or (4) subjecting a compound of the formula:

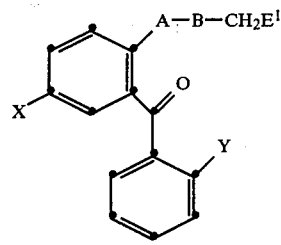

(wherein X, Y, —A—B—, and $E^1$ are the same as mentioned above) to reaction with an alcohol in the presence of potassium iodide and a base in an inert solvent.

More particularly, the preparations of the compounds [I] are as follows:

(1) In case of Z=H, D=O, and

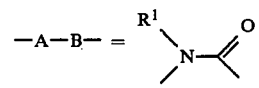

Reaction Scheme A

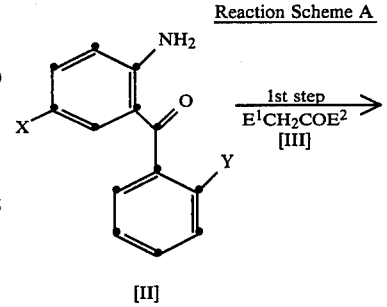

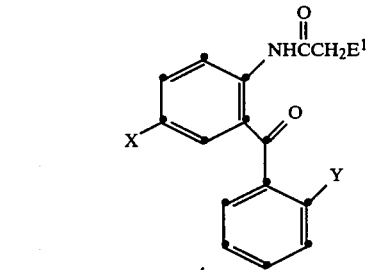

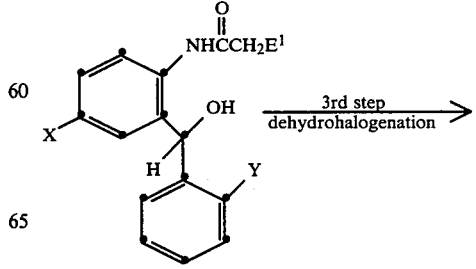

-continued
Reaction Scheme A

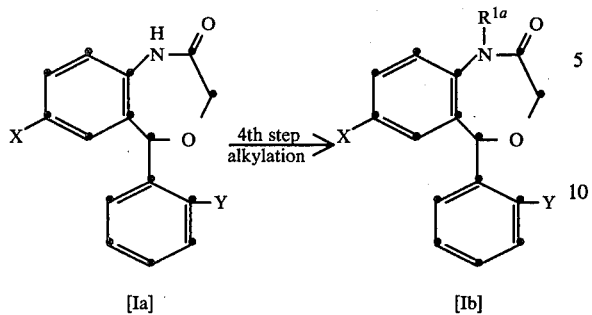

(wherein
X and Y are the same as mentioned above;
$R^{1a}$ is $C_1$ to $C_3$ alkyl; and
$E^1$ and $E^2$ each is the same or different halogen.)

(First Step)

This step can be carried out by reacting the starting materials [II] with the halogenoacetyl halogenides[III] in a suitable solvent such as benzene or pyridine in a manner for the acid amide formation. This step is preferably effected under heating at nearly the boiling point of the solvent. Representative of the halogenoacetyl halogenides [III] are chloroacetyl chloride, bromoacetyl bromide, and the like. It is preferred to employ an equal or excess amount of the halogenoacetyl halogenides to 1 mole of the starting compounds [II]. This reaction may be accelerated by addition of a suitable base such as triethylamine, quinoline, pyridine and the like. The starting materials [II] are described in J. Org. Chem., 26, 4488 (1961) by L. H. Sternbach et al.

(Second step)

This step involves reduction of carbonyl groups and can be readily carried out in a conventional manner. Thus, the reaction may be carried out by reducing the compounds [IV] with a reducing agent in a suitable inert solvent under cooling at a temperature below room temperature. Representative reducing agents are metal hydrides such as sodium borohydride, lithium borohydride, lithium aluminium hydride, diborane and the like. Representative of inert solvents are dimethylformamide, hexamethylphosphoric triamide, and the like.

(Third step)

This step is the dehydrohalogenating reaction and can be readily carried out in the presence of a base in a suitable solvent while refluxing under heating. Representative of bases are alkali metal hydroxide, alkaline earth metal hydroxide, and alkali metal alcoholate. Representative of solvents are ethanol, dioxane, benzene, dimethylsulfoxide, and the like.

(Fourth step)

This step can be carried out by reacting the compounds [Ia] with alkylating agents in the presence of a base such as sodium hydride in a conventional manner for alkylation of amines or amides. Representative alkylating agents are alkyl halides, alkyl esters of sulfuric acid, and the like. This reaction is ordinarily effected in a suitable inert solvent under heating. Representatives of inert solvents are ethanol, benzene, dimethylformamide, dioxane, and the like.

(2) In case of Z=H, D=O, and

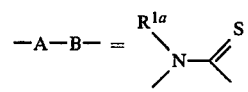

Reaction Scheme B

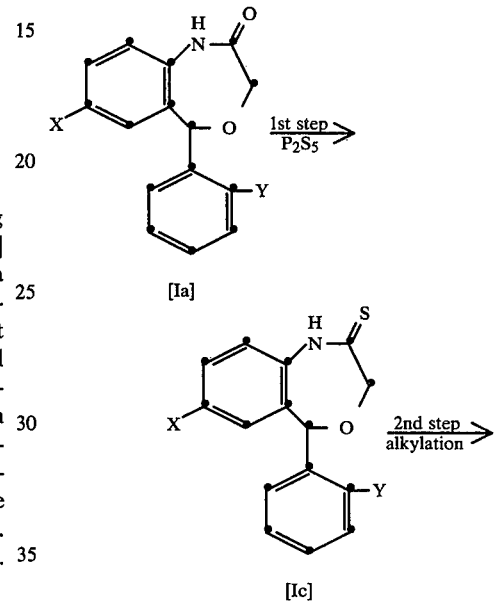

(wherein X, Y, and $R^{1a}$ are the same as mentioned above.)

(First step)

This step can be carried out by reacting the compounds [Ia] (prepared in the above Reaction Scheme A) with phosphorus pentasulfide in the presence of a base in a suitable solvent at about 60° to 120° C., preferably about 100° C. A base is employed as reaction accelerator and representative bases are alkali carbonate, alkali hydrogencarbonate, and the like. Representative solvents are diglyme, dioxane, hexamethylphosphoric triamide, dimethylsulfoxide, tetrahydrofuran, and the like.

(Second step)

This step can be carried out in the same manner as in the 4th step of Reaction Scheme A.

(3) In case of Z=H, D=S, and

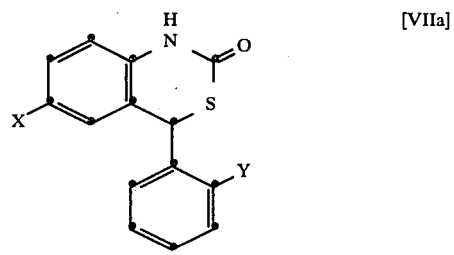

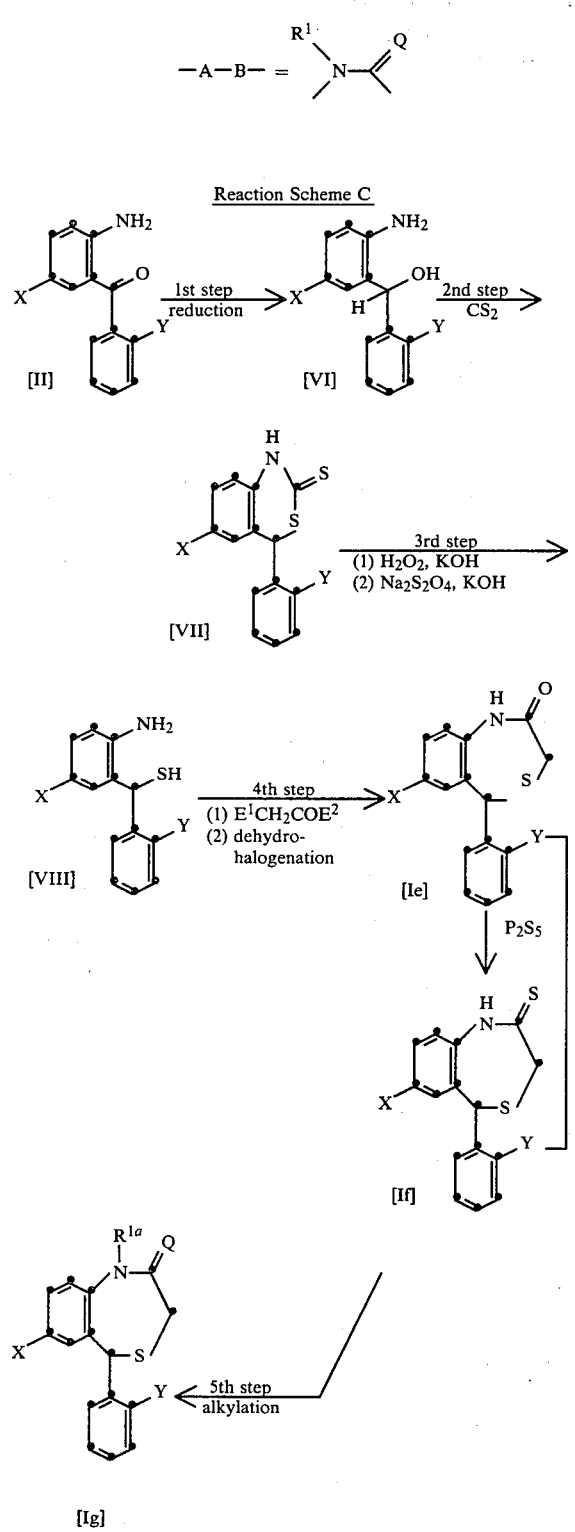

(wherein X, Y, Q, $R^{1a}$, $E^1$, and $E^2$ each has the same meaning as mentioned above.)

(First step)

This step can be carried out in the same manner as in the 2nd step of Reaction Scheme A.

(Second step)

This step can be carried out by reacting the benzhydrol compounds [VI] with carbon disulfide in the presence of a base in a solvent such as aqueous alcohols and the like while refluxing under heating. It is preferred to employ alkali metal hydroxide such as sodium hydroxide and potassium hydroxide as a base.

(Third step)

This step consists of two reactions.

The thiocarbonyl compounds [VII] are oxidized with hydrogen peroxide in the presence of alcoholic potassium hydroxide in a solvent such as ethanol at room temperature or under cooling to give compounds of the formula:

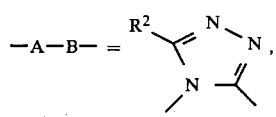
[VIIa]

(wherein X and Y each is the same as mentioned above) and then the latter is treated with sodium dithionite while refluxing under heating to give the mercaptan compounds [VIII].

(Fourth step)

This step also consists of two reactions. One is the reaction with halogenoacetyl halogenide and the other is cyclization by dehydrohalogenation. These two reactions can be carried out by the same methods as in the 2nd step and 3rd step of Reaction Scheme A, respectively.

(Fifth step)

This step is N-alkylation and can be carried out in the same manner as in the 4th step of Reaction Scheme A. The thioamide compounds [If] may be obtained by treating the corresponding amides [Ie] with phosphorus pentachloride.

(4) In case of Z=H, $$-A-B- = \text{(structure)}$$

and $R^2$=alkyl

Reaction Scheme D

-continued

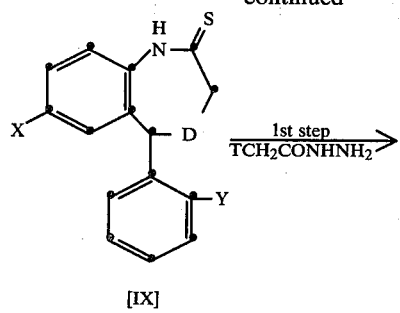

[IX]

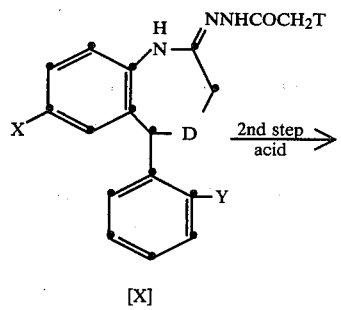

[X]

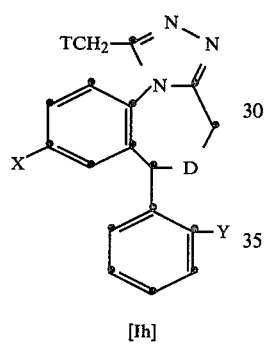

[Ih]

(wherein
X, Y, and D each is the same as mentioned above; and T is hydrogen or alkyl.)

(First step)

This step can be carried out by reacting the compounds [IX] (prepared in Reaction Scheme B or C) with alkanoylhydrazines in a conventional manner for the aminohydrazones formation. This reaction is oridinarily carried out in a suitable solvent such as chloroform, dimethylformamide, and the like at room temperature or under cooling.

(Second step)

The objective triazolo compound can be formed by heating the compounds [X] in the presence of an acid. Representative acids are acetic acid, propionic acid, benzoic acid, and the like.

(5) In case of Z=H,

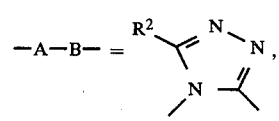

and $R^2$ = α-aminoalkyl

Reaction Scheme E

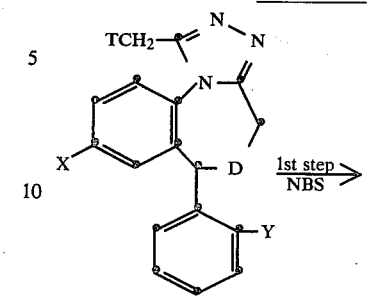

[Ih]

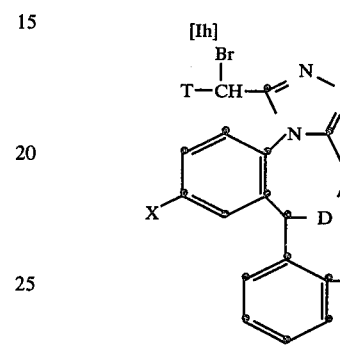

[XI]

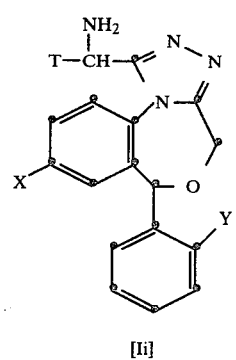

[Ii]

(wherein X, Y, D, and T each is the same as mentioned above.)

(First step)

This step can be carried out by reacting the compounds [Ih] (prepared in Reaction Scheme D) with N-bromosuccinimide (hereinafter referred to as "NBS"). Preferably, this reaction is carried out in carbon tetrachloride under refluxing. N-Bromoacetamide may be employed in place of NBS.

(Second step)

This step may be carried out by reacting the compounds [XI] with sodium azide to give the azides followed by reduction. The reduction may be readily effected by treating with hydrochloric acid or sodium hydroxide over stannous chloride.

Alternatively, the objective compounds [Ii] may be obtained by reacting the compounds [XI] with sodium amide or potassium amide in liquid ammonia under cooling.

(6) In case of Z=H, D=O, and

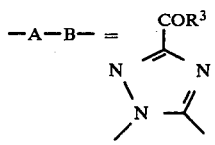

Reaction Scheme F

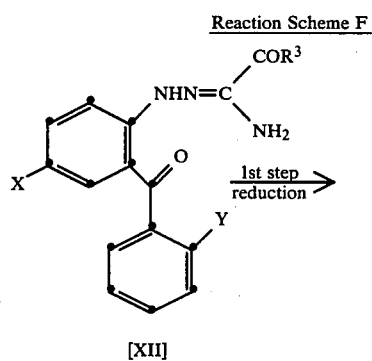

[XII]

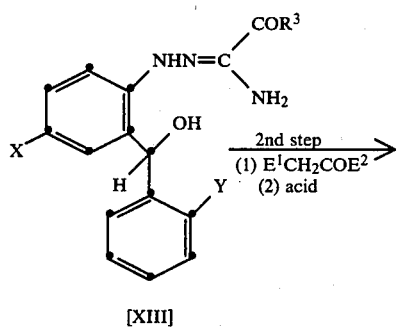

[XIII]

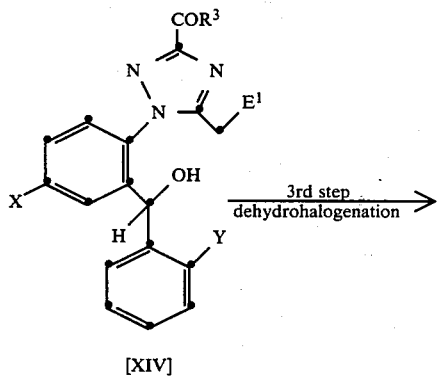

[XIV]

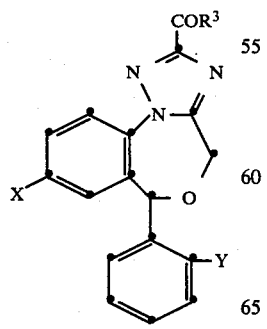

[Ij]

(wherein X, Y, $R^3$, and $E^1$ each is the same as mentioned above.)

(First step)

This step can be carried out in the same manner as in the 2nd step of Reaction Scheme A. The starting compounds [XII] may be prepared by the method described in Japanese Unexamined Patent Publication No. 148078/1977.

(Second step)

This step may be carried out by reacting the benzhydrol compounds [XIII] with the halogenoacetyl halogenides in the same manner as in the 1st step of Reaction Scheme A followed by heating in the presence of an acid such as acetic acid, propionic acid, benzoic acid, and the like.

(Third step)

This step is cyclization to the oxazepine ring and may be achieved in the same manner as in the 3rd step of Reaction Scheme A.

(7) In case of Z=H,

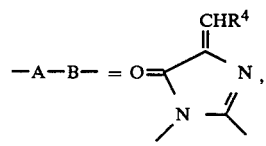

$R^4$=dialkylamino

Reaction Scheme G

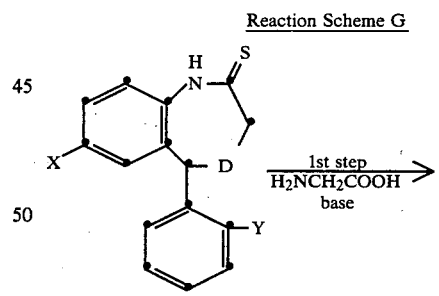

[IX]

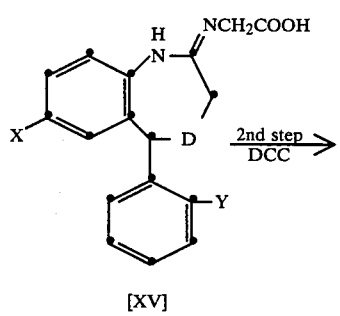

[XV]

-continued

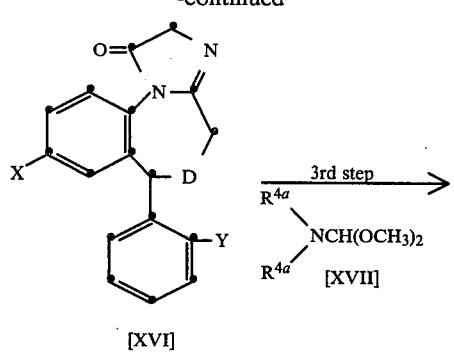

[XVI]

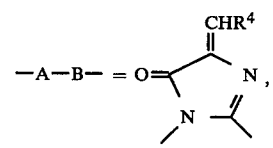

and $R^4$=alkylpiperazino

Reaction Scheme H

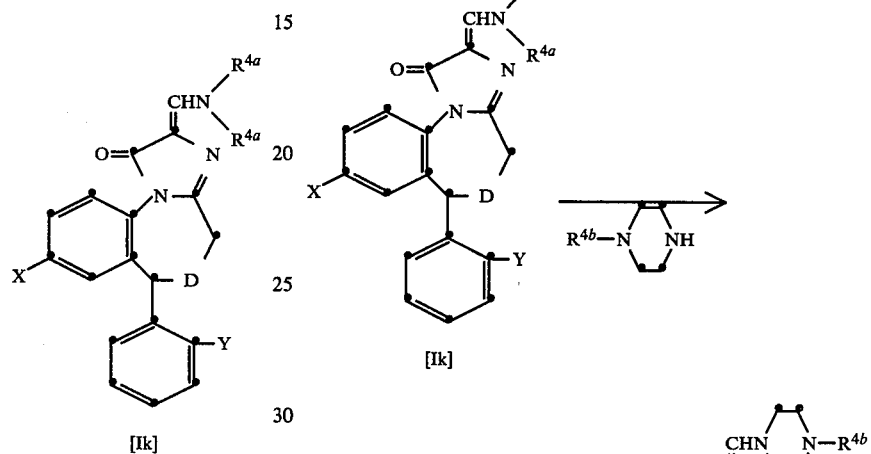

(wherein
X, Y, and D each is the same as mentioned above; and $R^{4a}$ is alkyl.)

(First step)

This step can be carried out by reacting the thioamide compounds [IX] with glycine in the presence of a base such as triethylamine in a conventional manner for the amidines formation. Preferably, this reaction is effected in a suitable solvent such as dimethylformamide, chloroform, benzene, and the like at room temperature or under heating (at a temperature below about 100° C.).

(Second step)

This step can be carried out by reacting the compounds [XV] with a condensating agent such as dicyclohexylcarbodiimide (hereinafter referred to "DCC") in a suitable solvent at room temperature. Representative of solvents are dimethylformamide, dimethylsulfoxide, chloroform, and the like.

(Third step)

This step can be carried out by reacting the active methylene compounds [XVI] with the acetal compounds [XVII] in the presence of an acid acceptor such as triethylamine. Preferably, this reaction is carried out in a suitable inert solvent at room temperature. Representative inert solvents are benzene, toluene, dimethylsulfoxide, diglyme, chloroform, and the like.

(8) In case of Z=H, (wherein
X, Y, D, and $R^{4a}$ each is the same as mentioned above; and
$R^{4b}$ is alkyl.)

This is an exchange reaction of substituents, and can be carried out by reacting the compounds [Ik] (prepared in Reaction Scheme G) with 4-alkylpiperazine in a suitable solvent under heating at the boiling point of the solvent. Representative solvents are benzene, toluene, chloroform, dimethylsulfoxide, tetrahydrofuran, and the like.

(9) In case of Z=H and

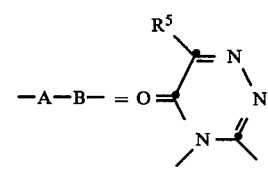

Reaction Scheme I

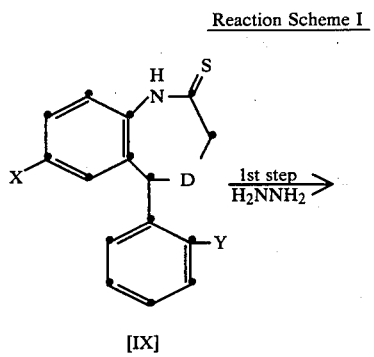

[IX]

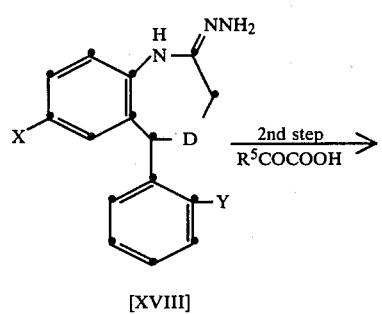

[XVIII]

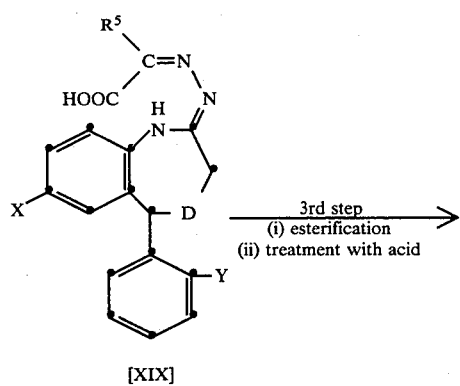

[XIX]

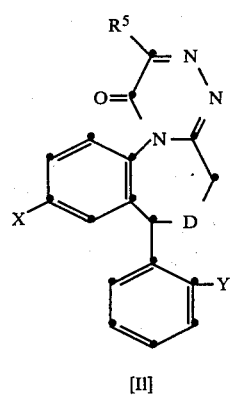

[II]

(wherein X, Y, D, and $R^5$ each is the same as mentioned above.)

(First step)

This step is an ordinary amidorazone formation and can be carried out in the same manner as in the 1st step of Reaction Scheme D.

(Second step)

This step can be carried out by condensation of the amidorazones [XVIII] and α-keto acids in a suitable solvent under heating at nearly the boiling point of the solvent. Representative solvents are ethanol, dimethylformamide, benzene, and the like.

(Third step)

This step consists of esterifying the compounds [XIX] and treating the resulting ester with an acid for cyclization. The esterification includes the methyl esterification by addition of diazomethane. This reaction can be effected in a suitable solvent at room temperature. Representative solvents are methanol, ethanol, benzene, methylene chloride, dimethylsulfoxide, ether, tetrahydrofuran, and the like. These solvents may be employed singly or as a mixture of two or more of them. The cyclization may be carried out by treating the ester of the compounds [XIX] with an acid such as acetic acid while refluxing under heating.

(10) In case of Z=alkoxy or dialkylaminoalkoxy

Reaction Scheme J

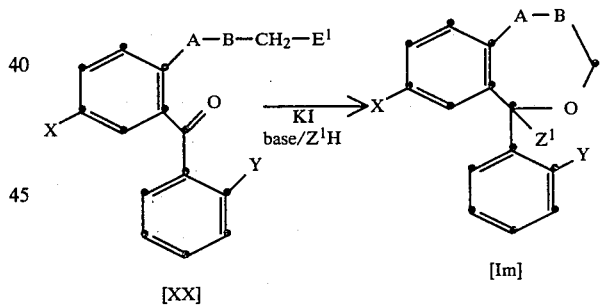

[XX]   [Im]

(wherein

A, B, X, Y, and $E^1$ are the same as mentioned above; and $Z^1$ is $C_1$ to $C_3$ alkoxy or $C_3$ to $C_9$ dialkylaminoalkoxy)

This reaction may be carried out by reacting the benzophenone compounds [XX] with alcohols such as ethanol in the presence of potassium iodide and a base while refluxing under heating. It is preferred to employ metallic sodium or sodium hydride as a base. The starting materials [XX] are described in Japanese Unexamined Patent Publication No. 83469/1977.

The following Table 1 shows $ED_{50}$ values in the antipentylenetetrazol test and rotarod performance test, and $LD_{50}$ values.

TABLE 1

| —A—B— | D | X | Y | Z | ED$_{50}$*[1] (mg/kg) anti-pentylene-tetrazol test*[2] | ED$_{50}$*[1] (mg/kg) rotarod performance test | LD$_{50}$*[3] |
|---|---|---|---|---|---|---|---|
| CH$_3$-C(=N-N)-N=CH- (methyl triazole) | O | Cl | Cl | H | 0.74 | 30.6 | >1000 |
| H$_2$NCH$_2$-C(=N-N)-N=CH- | " | " | " | OC$_2$H$_5$ (½ succinate) | 1.14 | 33.5 | >1000 |
| " | " | " | " | H (hydrobromide) | 2.49 | 24.1 | >1000 |
| H-C(-N(CH$_3$)$_2$)=C(-C=O)-N-N=CH- | " | " | " | H (hydrobromide) | 1.6 | 73.5 | >1000 |
| H-C(-N-morpholine/piperazine-N-CH$_3$)=C(-C=O)-N-N=CH- | " | " | " | H (hydrobromide) | 3.28 | >100 | >1000 |
| CH$_3$-C(=N-N)-C(=O)-N-N=CH- | " | " | " | H (hydrobromide) | 0.75 | 24.5 | >1000 |
| medazepam | | | | | 4.76 | 103.7 | >1000 |
| diazepam | | | | | 1.2 | 13.4 | >1000 |

*[1] test animal: SLC ddY male mouse, 20–24 g of body weight
*[2] pentylenetetrazol was preliminarily administered at a dose of 125 mg per 1 kg of body weight in subcutaneous injection.
*[3] test animal: DS male mouse, 20–24 g of body weight As shown in Table 1, the compounds [I] of this invention have excellent central nervous system actions and may be employed as sedatives, hypnotics, muscle relaxants, anticonvulsants, autonomic drugs, and the like.

The compounds [I] of this invention can be used in a wide variety of oral or parenteral dosage forms solely or in admixture with other co-acting substances. The pharmaceutical compositions may be a mixture of 0.01 to 99% of the compounds [I] with a pharmaceutical carrier or carriers which can be a solid material or liquid material in which the compounds [I] are soluble, dispersible, or suspendable. They can be in a unit dosage form. The solid compositions can be in forms of tablets, powder, dry syrups, troches, granules, capsules, pills, suppositories, or like solid preparation. The liquid compositions can be in forms of injections, ointments, dispersions, inhalant, suspensions, solutions, emulsions, syrups, or elixirs. All of diluents (e.g. starch, sucrose, lactose, calcium carbonate, kaolin); bulking agents (e.g. lactose, sugar, salt, glycine, starch, calcium carbonate, calcium phosphate, kaolin, bentonite, talc, sorbitol); binders (e.g. starch, acacia, gelatin, glucose, sodium arginate, tragacanth, carboxymethylcellulose, sorbitol, polyvinylpyrrolidone); disintegrators (e.g. starch, agar, carbonates, sodium laurylsulfate), lubricant (e.g. stearic acid, talc, paraffin, boric acid, silica, sodium benzoate, polyethylene glycol, cacao oil, magnesium sulfate); emulsifying agents (e.g. lecithin, sorbitan monooleate, acacia); suspending agents (e.g. sorbitol, methylcellulose, glucose, sugar, gelatin, hydroxyethylcellulose, carboxymethylcellulose, aluminium stearate gel, hydrogenated fats); solvents (e.g. water, peanut oil, sesame oil, methyl oleate); preservatives (e.g. methyl or ethyl p-hydroxybenzoate, sorbic acid), edible coloring agents, aromatic substances, solubilizing agents, buffers, stabilizing agents, dispersing agents, wetting agents, antioxidants, and the like can be used in the conventional manners as far as they do not act adversely on the compounds [I].

The compounds [I] of this invention are conveniently used as solutions for intravenous, intramusclar, or subcutaneous injections according to a conventional method. The compounds [I] can be dissolved in an aqueous or oily solvent for injection to give an injectable solution in an ampoule. In order to preserve the injectable preparation for a long period of time, it is appropriate to make a vial preparation containing crystals, powder, microcrystals, or lyophilizate of the compounds [I]. The vial preparation may be dissolved or suspended in the said solvents for injection immediately before use. The preparation may contain said preservatives.

The compounds [I] of this invention may be administered at a daily dose of about 1 to 40 mg to adult humans. The compounds [I] may be daily administered once or 2 to 3 times in divided portions. It is appropriate to increase or decrease the dosage according to the purpose of the application, the conditions, anamnesis, and age of the patients.

The following examples are provided to further illustrate this invention.

EXAMPLE 1

Preparation of 1-methyl-6-(2-chlorophenyl)-8-chloro-4H,6H-(1,2,4)triazolo[4,3-a][4,1]benzoxazepine

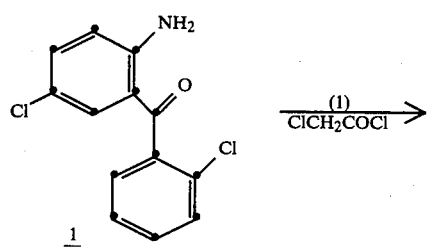

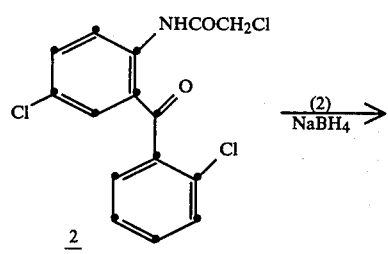

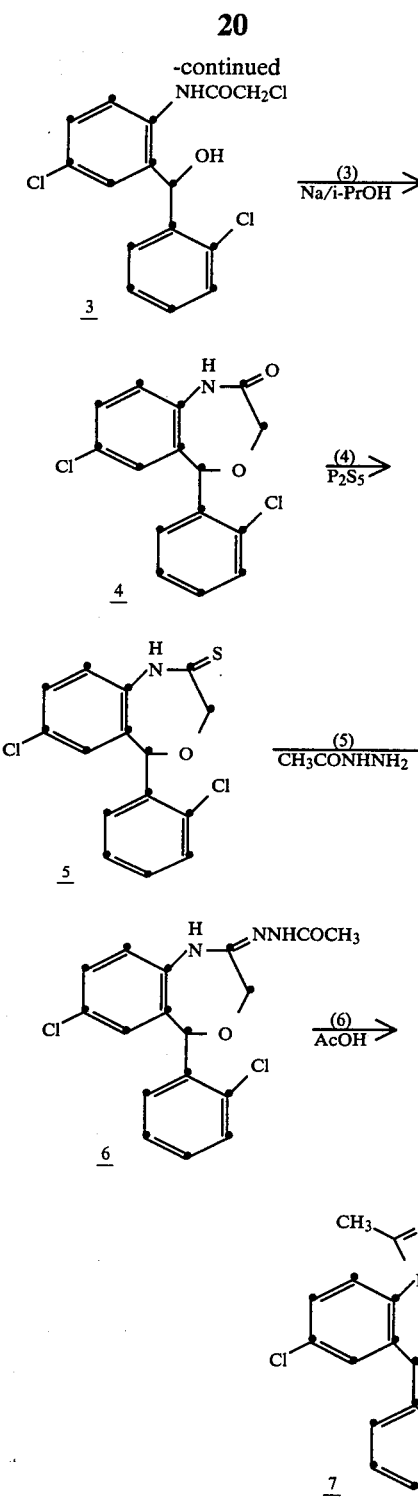

(1) Compound 1 (5.4 g) is dissolved in a mixture of 2.0 ml of chloroacetyl chloride and 100 ml of anhydrous benzene, and the resulting solution is refluxed under heating on an oil bath for 4 hours and concentrated under reduced pressure. The residue is washed with n-hexane to give 6.8 g of Compound 2 as crude crystals in 97.8% yield. The crude product is recrystallized from ethyl acetate.

mp. 160°–161.5° C.

Elemental Analysis (for $C_{15}H_{10}O_2NCl_3$): Calcd(%): C, 52.58; H, 2.94; N, 4.09; Cl, 31.05. Found(%): C, 52.50; H, 2.83; N, 4.10; Cl, 30.97.

(2) To a solution of 4.0 g (11.67 mmoles) of Compound 2 in 50 ml of dimethylformamide cooled at 0° C. is added 432 mg (11.7 mmoles) of a lump of sodium borohydride with stirring, and the mixture is stirred for 2 hours, while keeping the internal temperature at 0° to 5° C. The reaction mixture is poured into 500 ml of water, which is acidified with 1 N hydrochloric acid and extracted with ethyl acetate. The extract is washed with water, dried, and evaporated. The resulting residue (4.1 g) is washed with 30 ml of ether to give 2.9 g of pure crystalline Compound 3. From the ethereal washings 639 mg of Compound 3 is also obtained and recrystallized from ethyl acetate.

Total yield: 88%
mp. 154°–155° C.

Elemental Analysis (for $C_{15}H_{12}O_2NCl_3$): Calcd(%): C, 52.27; H, 3.51; N, 4.06; Cl, 30.87. Found(%): C, 52.38; H, 3.44; N, 4.03; Cl, 30.57.

(3) To a boiling solution of 540 mg (23 mmoles) of sodium in 50 ml of isopropanol is dropwise added a solution of 2.9 g (8.4 mmoles) of Compound 3 in 100 ml of absolute isopropanol, and the mixture is refluxed under heating for 1 hour and concentrated to about 50 ml. The residue is diluted with 100 ml of water and acidified with concentrated hydrochloric acid. The resulting precipitate is collected by filtration, washed with water, dissolved in chloroform, dried, and concentrated. The residue is washed with ether to give 2.0 g of Compound 4 in 80.9% yield, which is recrystallized from acetone.

mp. 236°–237° C.
IR: $\nu_{max}^{Nujol}$ 3200, 3050, 1670, 1580 cm$^{-1}$.

Elemental Analysis (for $C_{15}H_{11}O_2NCl_2$): Calcd(%): C, 58.46; H, 3.60; N, 4.54; Cl, 23.01. Found(%): C, 58.39; H, 3.62; N, 4.62; Cl, 23.31.

(4) Compound 4 (914 mg; 2.97 mmoles), 1.516 g (6.82 mmoles) of phosphorus pentasulfide and 572 mg (6.8 mmoles) of sodium hydrogencarbonate are dissolved in 40 ml of diglyme, and the resulting solution is stirred under heating at 100° C. on an oil bath for 2 hours, poured into 600 ml of water, and extracted with ethyl acetate. The extract is washed with water, dried, and evaporated. The resulting light yellow crystals (1.762 g) are purified on chromatography (silica gel/methylene chloride) to give 926 mg of Compound 5 in 96.3% of yield.

mp. 159°–160° C.
MS spectrum: m/e=323
IR: $\nu_{max}^{Nujol}$ 3180, 1580, 1530, 1120 cm$^{-1}$.

Elemental Analysis (for $C_{15}H_{11}ONSCl$): Calcd(%): C, 55.56; H, 3.42; N, 4.32; S, 9.89; Cl, 21.87. Found(%): C, 55.58; H, 3.36; N, 4.25; S, 9.80; Cl, 22.12.

(5) Compound 5 (894 mg; 2.8 mmoles) and acetylhydrazine (600 mg; 8.1 mmoles) are dissolved in 30 ml of chloroform, and the solution is stirred at room temperature for 2 hours. The resulting precipitate is collected by filtration and washed with a small amount of ethyl acetate to give 1.005 g of Compound 6.

(6) A solution of 1.5 g of Compound 6 in 20 ml of acetic acid is refluxed under heating for 2 hours and evaporated under reduced pressure. The residue is dissolved in water, made alkaline with 1 N aqueous sodium hydroxide solution, and extracted with chloroform. The extract is washed with water, dried, and evaporated. The residue is washed with a small amount of ether to give 1.272 g of Compound 7 in 89.2% yield.

mp. 229° C.
NMR: $\delta^{CDCl_3}$ 2.3(s,3H), 4.47, 5.19(AB, J=13 Hz,2H), 5.62(s,1H).

Elemental Analysis (for $C_{17}H_{13}ON_3Cl_2$): Calcd(%): C, 58.97; H, 3.78; N, 12.14; Cl, 20.84. Found(%): C, 58.96; H, 3.78; N, 12.42; Cl, 20.25.

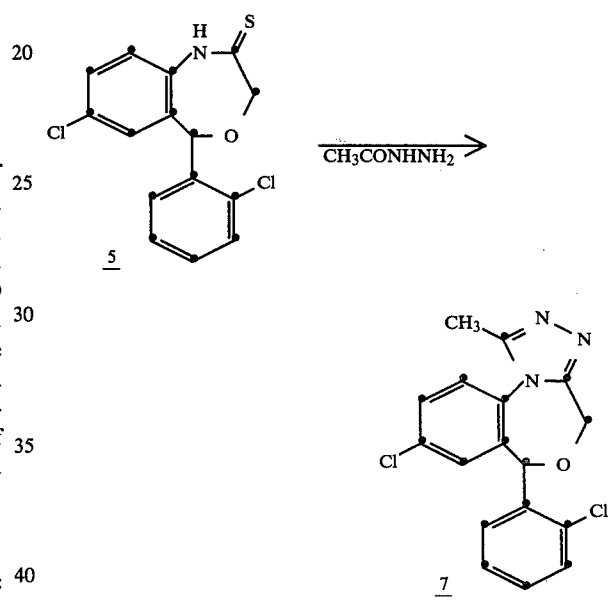

A solution of 32 mg of Compound 5 and 53 mg of acetylhydrazine in 3 ml of pyridine is refluxed under heating on an oil bath for 2 hours and evaporated under reduced pressure. The residue is purified on thin layer chromatography (silica gel/ethyl acetate) to give 24 mg of Compound 7 in 70.2% yield.

EXAMPLE 2

Preparation of 1-aminomethyl-6-(2-chlorophenyl)-8-chloro-4H,6H-(1,2,4)triazolo[4,3-a][4,1]benzoxazepine

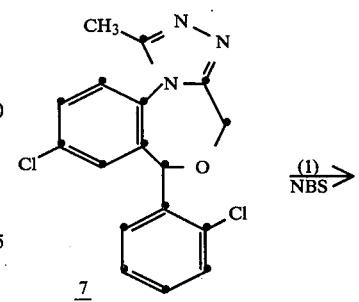

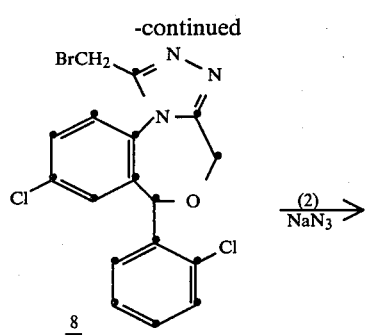

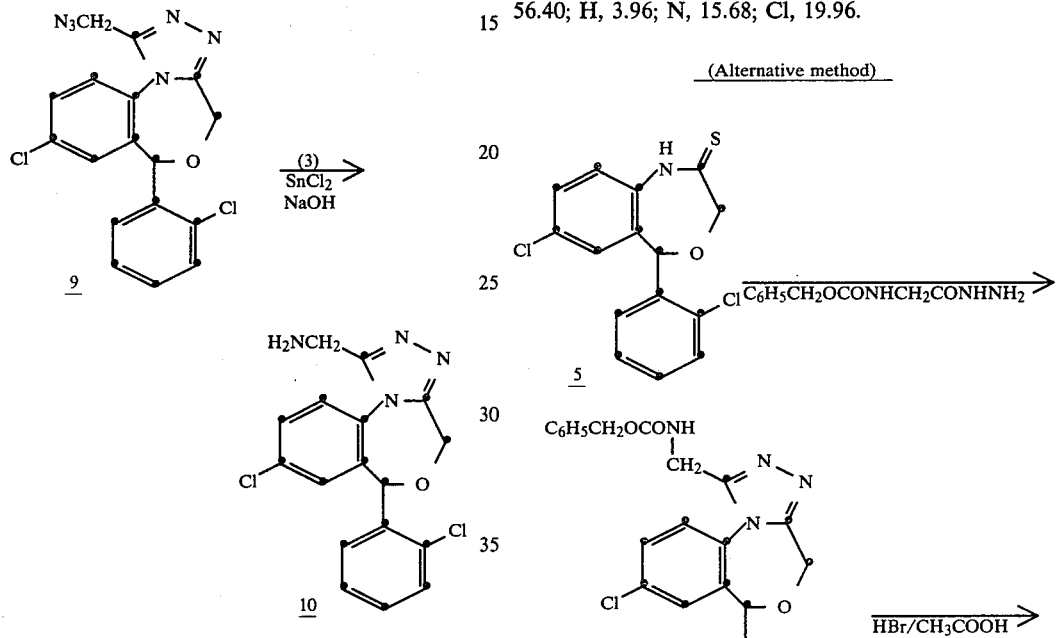

for 2 hours, diluted with 30 ml of water, saturated with sodium chloride, and extracted with ethyl acetate. The extract is washed with water, dried and evaporated. The residue is purified on thin layer chromatography (silica gel/ethyl acetate-methanol (20:5)) to give 38 mg of Compound 10.

mp. 198°–200° C.

NMR: $\delta^{d6\text{-}DMSO}$ 4.12 (brs, 2H), 4.52, 5.13 (AB, J=14 Hz, 2H), 5.58 (s, 1H).

MS spectrum: m/e=360

Elemental Analysis (for $C_{17}H_{14}ON_4Cl_2$): Calcd(%): C, 56.52; H, 3.91; N, 15.51; Cl, 19.63. Found(%): C, 56.40; H, 3.96; N, 15.68; Cl, 19.96.

(Alternative method)

(1) To a solution of 2.0 g (5.8 mmoles) of Compound 7 in 100 ml of carbon tetrachloride are added 1.1 g (6.2 mmoles) of N-bromosuccinimide and 2 mg of AIBN, and the mixture is stirred under heating on an oil bath for 20 minutes. The resulting precipitate is filtered off and the filtrate is mixed with 5% aqueous sodium thiosulfate solution, shaken, washed with water, dried and evaporated. The residue is purified on chromatography (silica gel/ethyl acetate) to give 505 mg of Compound 8 in 20% yield.

NMR: $\delta^{CDCl_3}$ 4.78 (ABq, J=13 Hz, 2H), 4.80 (ABq, J=13 Hz, 2H), 5.57 (s, 1H).

(2) Compound 8 (146 mg; 0.34 mmole) and sodium azide (44 mg; 0.68 mmole) are dissolved in 3 ml of dimethylformamide and the solution is refluxed under heating on an oil bath for 8 hours, diluted with 30 ml of water and then extracted with ethyl acetate. The extract is washed with water, dried and evaporated. The residue is purified on thin layer chromatography (silica gel/ethyl acetate) to give 41 mg of Compound 9.

IR: $\nu_{max}^{CHCl_3}$ 2090 cm$^{-1}$.

NMR: $\delta^{CDCl_3}$ 4.73 (Abq, J=12 Hz, 2H), 4.83 (ABq, J=14 Hz,2H), 5.60(s, 1H).

(3) To a solution of 40 mg of Compound 9 in 2 ml of ethanol is added a solution of 50 mg of stannous chloride dihydrate in 1 ml of 1 N aqueous sodium hydroxide solution, and the mixture is stirred at room temperature (1) To a solution of 1.8 g (5.56 mmoles) of Compound 5 in 50 ml of chloroform is added 1.3 g (5.82 mmoles) of benzyloxycarbonylaminoacetylhydrazine, and the mixture is stirred at room temperature for 16 hours, refluxed under heating on an oil bath with stirring for 10 hours, and then concentrated. The residue is dissolved in 20 ml of ether, and the insoluble materials are filtered off. The filtrate is evaporated to dryness and the resulting oily product is purified on column chromatography (silica gel/ethyl acetate) to give 2.0 g of Compound 11 as foamy product in 73% yield.

NMR: $\delta^{CDCl_3}$ 5.00(s, 2H), 5.60(s, 1H), 4.35+5.12(Abq, J=12 Hz, 2H), 4.57+4.90(ABq, J=14 Hz, 2H).

(2) A solution of 2.0 g of Compound 11 in 40 ml of 30% hydrobromic acid-acetic acid is stirred at room temperature for 20 hours and mixed with 200 ml of anhydrous ether. The precipitated crystals are collected by filtration and washed with ether. A part of the obtained product (253 mg) is shaken with a mixture of chloroform and 5% aqueous sodium hydrogencarbonate solution. The organic layer is separated, washed with water, dried and evaporated to give 189 mg of Compound 10, which is recrystallized from chloroform-ether.

EXAMPLE 3

Preparation of 1-methyl-6-(2-chlorophenyl)-8-chloro-4H,6H-(1,2,4)-triazolo[4,3-a][4,1]benzothiazepine

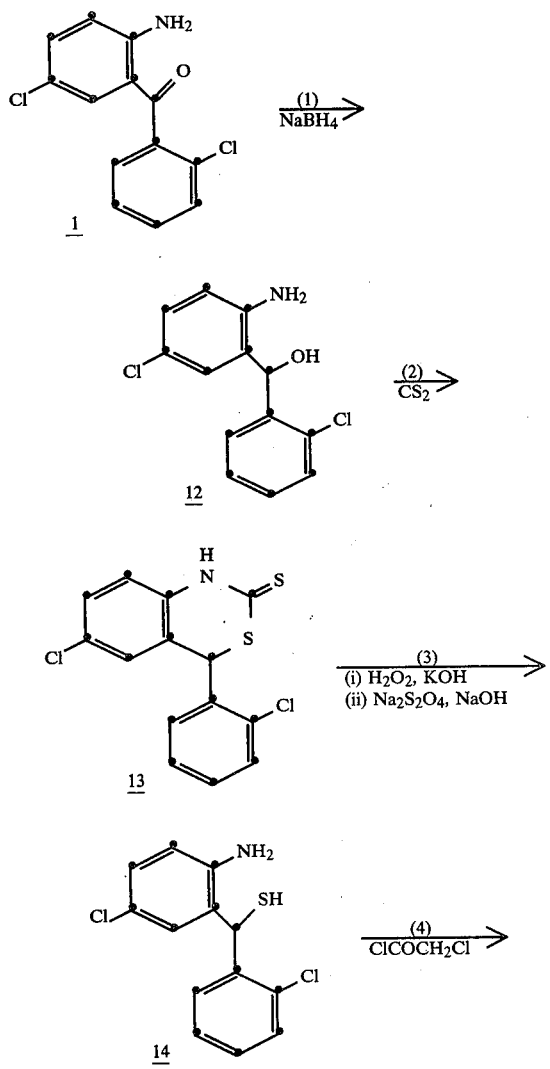

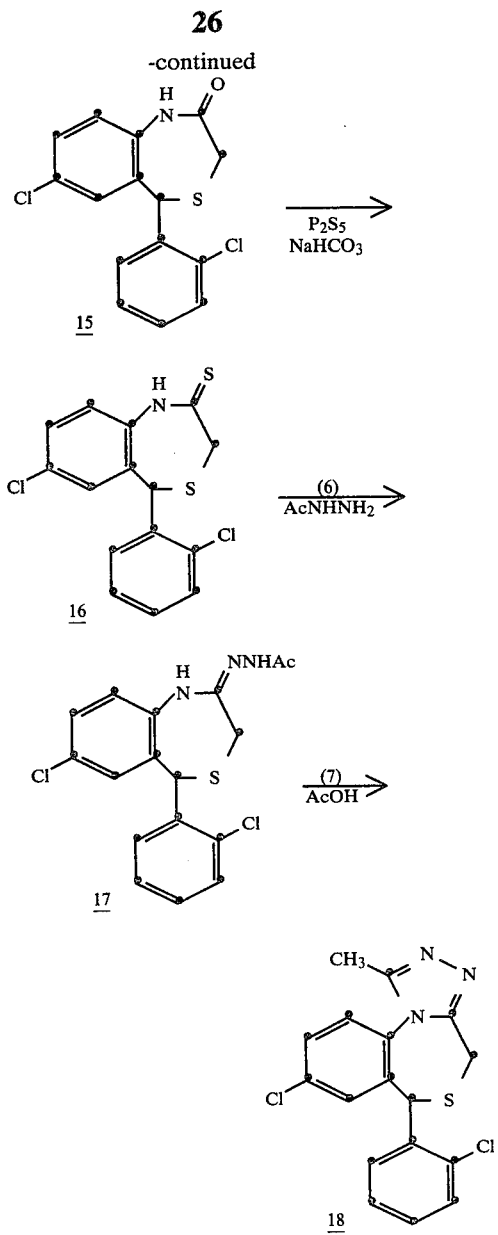

(1) To a solution of 53.2 g of Compound 1 in 115 ml of tetrahydrofuran is added a solution of 19.6 g of sodium borohydride in a mixture of 450 ml of tetrahydrofuran and 75 ml of water at room temperature with stirring, and the mixture is stirred at the same temperature for 4 days. The excess amount of sodium borohydride is decomposed with concentrated hydrochloric acid and extracted with chloroform. The extract is washed with water, dried, and evaporated. The residue is crystallized from n-hexane to give 49.02 g of Compound 12 in 91.5% yield, which is recrystallized from ether-n-hexane.

mp. 101°–104° C.

(2) To a mixture of 240 ml of ethanol, 30 ml of water, 30 ml of carbon disulfide, and 14.4 g (0.257 mole) of potassium hydroxide is added 40.2 g (0.15 mole) of Compound 12, and the resulting mixture is refluxed for 18 hours, concentrated to about 60 ml, poured into 600 ml of iced water, and adjusted at pH 4 to 5 with hydrochloric acid. The precipitated crystals are collected by filtration and washed with water to give 31.9 g of Compound 13 in 65% yield, which is recrystallized from methylene chloride.

mp. 207°–211° C. (d)

Elemental Analysis (for $C_{14}H_{19}NS_2Cl_2$): Calcd(%): C, 51.54; H, 2.78; N, 4.29; Cl, 21.73; S, 19.65. Found(%): C, 51.44; H, 2.66; N, 4.28; Cl, 1970; S, 21.75.

(3) To a solution of 31 g (0.095 mole) of Compound 13 in a mixture of 78 ml of 5 N aqueous potassium hydroxide solution and 600 ml of ethanol is dropwise added 234 ml of 30% hydrogen peroxide at a temperature below 20° C., and the resulting mixture is stirred at 10° C. for 1 hour and at room temperature for 18 hours, and after cooling, adjusted at pH 3 to 4 with 10% hydrochloric acid. A solution of 31 g of the resulting crystals and 2.1 g of sodium dithionite in 210 ml of 20% aqueous potassium hydroxide solution is refluxed for 4 hours, cooled, neutralized with acetic acid, and extracted with methylene chloride. The extract is washed with water, dried over sodium sulfate and evaporated under reduced pressure. The residue is purified on column chromatography (silica gel/methylene chloride) to give 8.7 g of Compound 14 as oily product in 31% yield.

NMR: $\delta^{CDCl_3}$ 2.25(d, J=6 Hz, 1H), 5.74(d, J=6 Hz, 1H), 3.85(br, 2H).

(4) To a solution of 8.7 g (0.0306 mole) of Compound 14 in 174 ml of ether are dropwise added 4.5 ml of chloroacetyl chloride and 50 ml of 2 N aqueous sodium hydroxide solution successively. The ether layer is separated, dried, and evaporated under reduced pressure. The residue is purified on column chromatography (silica gel/methylene chloride). The residue from Fraction No. 2 is crystallized and recrystallized from ether to give 2.65 g of Compound 15 as colorless needles in 27% yield.

mp. 214°–217° C.

Elemental Analysis (for $C_{15}H_{11}NCl_2OS$): Calcd(%): C, 55.57; H, 3.42; N, 4.32; Cl, 21.87; O, 4.93; S, 9.89. Found(%): C, 55.49; H, 3.40; N, 4.30; Cl, 21.87; O, 4.81; S, 9.86.

(5) To a solution of 1.744 g of Compound 15 in 40 ml of diglyme are added 1.29 g of phosphorus pentasulfide and 0.924 g of sodium hydrogencarbonate, and the mixture is stirred at 100° C. for 2 hours, poured into 100 ml of water and extracted with ethyl acetate. The extract is washed with water, dried, and evaporated under reduced pressure. The residue is treated on column chromatography (silica gel/methylene chloride) to give 0.63 g of Compound 16 as colorless prisms in 81% yield.

mp. 206°–210° C. (d)

Elemental Analysis (for $C_{15}H_{11}NCl_2S_2$): Calcd(%): C, 52.95; H, 3.26; N, 4.12; Cl, 20.84; S, 18.84. Found(%): C, 53.08; H, 3.26; N, 4.04; Cl, 20.36; S, 18.56.

(6) To a solution of 0.57 g (1.68 mmoles) of Compound 16 in 30 ml of chloroform is added 740 mg (10 mmoles) of acetylhydrazine, and the mixture is stirred at room temperature for 3 days to give 608 mg of crude Compound 17.

NMR: $\delta^{DMSO}$ 1.77(s, 3H), 3.30(br, 2H).

(7) A solution of 0.4 g (1.05 mmoles) of Compound 17 in 8 ml of acetic acid is refluxed for 2 hours, adjusted at pH 7.5 to 8 with aqueous sodium hydroxide solution under cooling and extracted with chloroform. The extract is washed with water, dried, and evaporated under reduced pressure. The residue is crystallized from ethanol to give 0.27 g of Compound 18 in 71% yield. This is recrystallized from ethyl acetate to give Compound 18 as colorless prisms.

mp. 286°–288° C. (d)

Elemental Analysis (for $C_{17}H_{13}N_3Cl_2S$): Calcd(%): C, 56.36; H, 3.62; N, 11.60; Cl, 19.57; S, 8.85. Found(%): C, 56.48; H, 3.56; N, 11.60; Cl, 19.33; S, 8.78.

EXAMPLE 4

Preparation of 1-oxo-2-(N,N-dimethylamino)methylidene-6-(2-chlorophenyl)-8-chloro-1,2-dihydro-4H,6H-imidazo[1,2-a][4,1]benzoxazepine

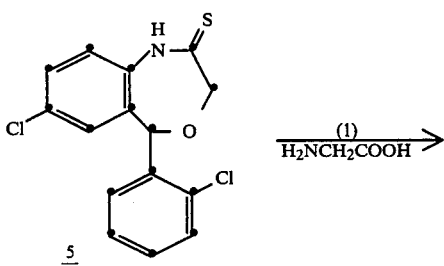

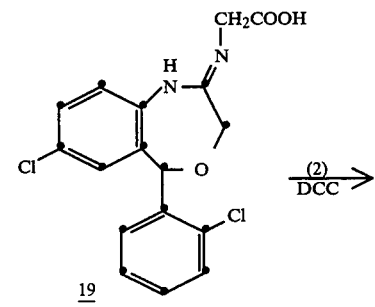

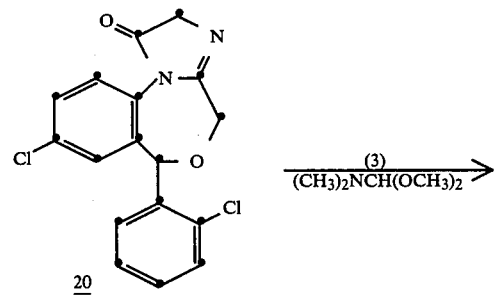

-continued

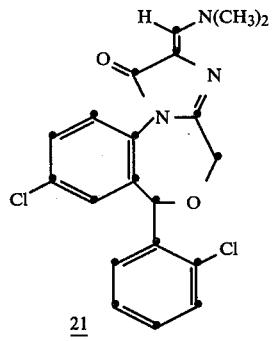

(1) A solution of 2.6 g (8 mmoles) of Compound 5, 2.0 g (26.6 mmoles) of glycine and 1.5 ml of triethylamine in 25 ml of dimethylformamide is stirred at room temperature for 3 days and at 60° C. for 3 hours, and then evaporated under reduced pressure. The residue is dissolved in 100 ml of water and adjusted at pH 4 with 4 N hydrochloric acid. The resulting precipitate is collected by filtration and recrystallized from ether-acetone to give 2.0 g of Compound 19 in 68.3% yield.

mp. 146°–148° C.

NMR: $\delta^{d6\text{-}DMSO}$ 3.96(brs, 2H), 4.23(ABq, J=12 Hz, 2H), 5.40(s, 1H).

(2) To a solution of 511 mg (1.4 mmoles) of Compound 19 in 8 ml of anhydrous dimethylformamide is added 350 mg (1.68 mmoles) of DCC, and the mixture is stirred at room temperature for 4 hours. The resulting precipitate is filtered off, and the filtrate is diluted with 100 ml of water and extracted with ethyl acetate. The extract is washed with water, dried and evaporated. The resulting oily residue (1.5 g) is purified on column chromatography (silica gel/ethyl acetate) to give 440 mg of Compound 20 as oily product in 90.6% yield.

IR: $\nu_{max}^{CHCl_3}$ 1755, 1650 cm$^{-1}$.

NMR: $\delta^{CDCl_3}$ 4.50(brs, 2H), 4.60 (Abq, J=14 Hz, 2H), 6.15(s, 1H).

(3) A solution of 341 mg (0.98 mmole) of Compound 20, 0.5 ml of triethylamine and 300 mg (2.5 mmoles) of N-dimethoxymethyl-N,N-dimethylamine in 10 ml of anhydrous benzene is stirred at room temperature for 1 hour and evaporated under reduced pressure. The residue is purified on column chromatography (silica gel/ethyl acetate) to give 289 mg of Compound 21 in 73% yield.

mp. 247°–248° C.

IR: $\nu_{max}^{Nujol}$ 1695, 1640 cm$^{-1}$.

NMR: $\delta^{CDCl_3}$ 3.25(s, 3H), 3.60(s, 3H), 4.60(AB, J=12 Hz), 5.97(s, 1H).

Elemental Analysis (for $C_{20}H_{17}O_2N_3Cl_2$): Calcd(%): C, 59.71; H, 4.26; N, 10.45; Cl, 17.63. Found(%): C, 59.92; H, 4.23; N, 10.51; Cl, 17.69.

EXAMPLE 5

Preparation of 1-oxa-2-(4-methylpiperazino)methylidene-6-(2-chlorophenyl)-8-chloro-1,2-dihydro-4H,6H-imidazo[1,2-a][4,1]benzoxazepine

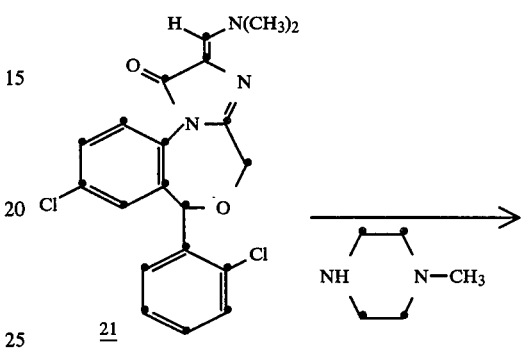

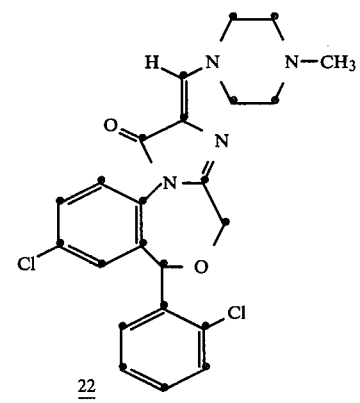

(1) A solution of 380 mg (0.9 mmole) of Compound 21 and 1.5 ml of N-methylpiperizine in 18 ml of anhydrous toluene is refluxed for 5 hours under heating on an oil bath and evaporated under reduced pressure. The residue (475 mg) is purified on column chromatography (silica gel/methanol) to give 342 mg of Compound 22 in 79% yield.

m.p. 233°–235° C.

IR: $\nu_{max}^{Nujol}$ 1689, 1630 cm$^{-1}$

NMR: $\delta^{CDCl_3}$ 2.47 (s,3H), 4.55 (AB, J=12 Hz, 2H), 5.92 (s, 1H).

Elemental Analysis (for $C_{23}H_{22}O_2N_4Cl_2$): Calcd(%): C, 60.40; H, 4.85; N, 12.25; Cl, 15.51. Found(%): C, 59.97; H, 4.75; N, 12.12; Cl, 15.96.

EXAMPLE 6

Preparation of 1-oxo-2-methyl-7-(2-chlorophenyl)-9-chloro-1,12-dihydro-5H,7H-(1,2,4)triazino[4,3-a][4,1]benzoxazepine

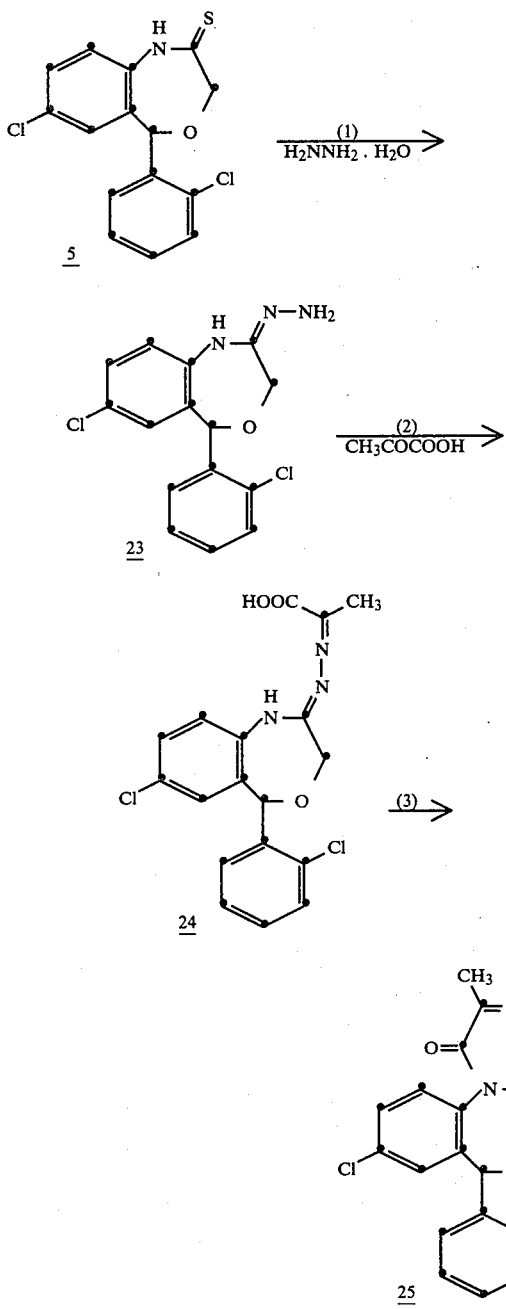

(1) To a suspension of 3.3 g of Compound 5 in 80 ml of ethanol is added 1.5 ml of hydrazine monohydrate with stirring. The resulting transparent solution is stirred at room temperature for 1 hour and concentrated to about 10 ml at a temperature below 35° C. under reduced pressure. The resulting precipitate is collected by filtration and washed with a small amount of ethanol to give 2.4 g of Compound 23. Compound 23 (700 mg) is also obtained from mother liquor.

Total yield: 94.5%
mp. 142°-150° C.
IR: $\nu_{max}^{Nujol}$ 3350, 1650 cm$^{-1}$
Elemental Analysis (for $C_{15}H_{13}ON_3Cl_2$): Calcd(%): C, 55.91; H, 4.07; N, 13.04. Found(%): C, 55.64; H, 3.90; N, 13.05.

(2) A solution of 1.6 g (5 mmoles) of Compound 23 and 600 mg (6.8 mmoles) of pyruvic acid in 40 ml of ethanol is refluxed for 5 minutes and stirred at room temperature for 2 hours. The precipitated crystals are collected by filtration and washed with a small amount of ethanol to give 1.613 g of Compound 24 as ethanol addition product.

mp. 131°-135° C.
IR:$\nu_{max}^{Nujol}$ 3240, 1738, 1625, 1590, 1565 cm$^{-1}$.
NMR:$\delta^{d_6-DMSO}$ 1.07(t,J=7 Hz,3H), 2.13(s,3H), 3.50(q,J=7Hz,2H), 4.50(brs,2H), 6.13(s,1H), 10.12(s,1H).

(3) To a solution of 1.6 g of the ethanol addition product of Compound 24 in a mixture of 10 ml of methanol and 40 ml of methylene chloride is added ether solution of diazomethane. After 10 minutes, the excess amount of diazomethane is evaporated off under atmospheric pressure. The residue is concentrated to about 10 ml under reduced pressure. The precipitated crystals (1.48 g) are collected by filtration, dissolved in 10 ml of acetic acid, refluxed under heating on an oil bath for 3 hours and evaporated under reduced pressure. The residue is dissolved in water, make alkaline with 5% aqueous sodium hydrogencarbonate solution and extracted with ethyl acetate. The extract is washed with water, dried, and evaporated. The residue is purified on chromatography (silica gel/ethyl acetate) to give 728 mg of Compound 25 in 53.5% yield.

mp. 175°-177° C.
IR: $\nu_{max}^{Nujol}$ 1690, 1575, 1525 cm$^{-1}$.
NMR: $\delta^{CDCl_3}$ 2.13(s,3H), 4.27+4.93(AB, J=12 Hz, 2H), 5.53(s,1H).
Elemental Analysis (for $C_{18}H_{13}O_2N_3Cl_2$): Calcd(%): C, 57.77; H, 3.50; N, 11.23; Cl, 18.95. Found(%): C, 57.53; H, 3.44; N, 11.21; Cl, 18.78.

EXAMPLE 7

Preparation of 1-methyl-2-oxo-5-(2-chlorophenyl)-1,2,3,5-tetrahydro-[4,1]benzoxazepine

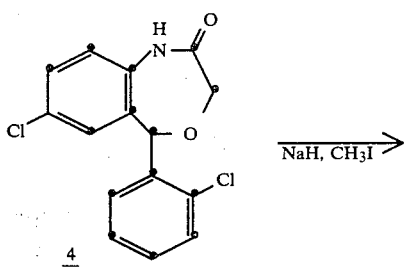

-continued

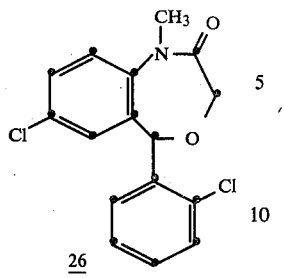

26

To a solution of 3.0 g (10 mmoles) of Compound 4 in 50 ml of anhydrous dimethylformamide are added 480 mg of solid sodium hydride at room temperature and 1.9 g of methyl iodide at 50° C., and the mixture is stirred for 4 hours, poured into ten times by volume of iced water, and extracted with ethyl acetate. The extract is washed with water, dried, and evaporated under reduced pressure. The residue is purified on column chromatography (silica gel/ether) to give 2.293 g of Compound 26 as viscous product in 73% yield.

IR: $\nu_{max}^{film}$ 1680 cm$^{-1}$

NMR: $\delta^{CDCl_3}$ 3.43(s, 3H), 4.17(AB, J=10 Hz, 2H), 6.02(s, 1H).

EXAMPLE 8

Preparation of 1-benzyl-2-oxo-5-ethoxy-5-(2-chlorophenyl)-7-chloro-1,2,3,5-tetrahydro[4,1]benzoxazepine

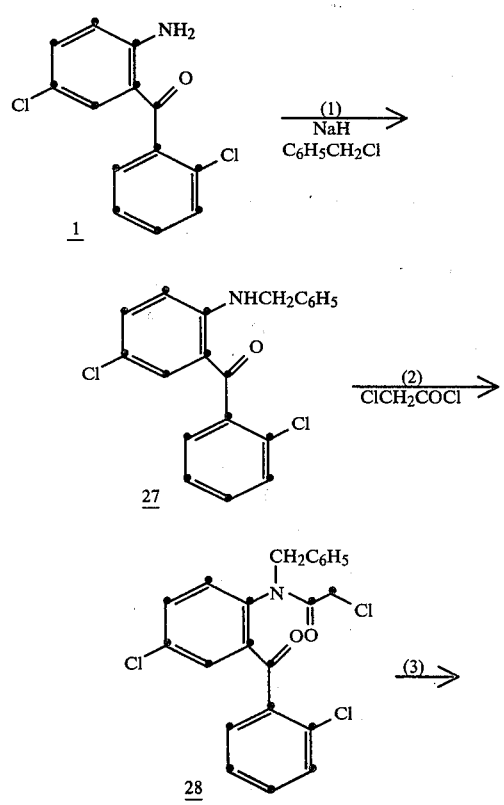

-continued

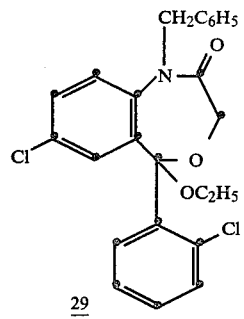

29

(1) Compound 1 (2.7 g) is dissolved in 20 ml of anhydrous dimethylformamide and the solution is cooled to −10° C. After the addition of sodium hydride (50% oily dispersion) (480 mg), the mixture is stirred at the same temperature for 15 minutes. A solution of 1.4 ml of benzyl bromide in 5 ml of dimethylformamide is dropwise added thereto. The reaction mixture is slowly warmed to 0° C., stirred for 3 hours, poured into iced water and extracted with ethyl acetate. The extract is washed with water, dried, and evaporated. The residue (3.5 g) is purified on column chromatography (silica gel/methylene chloride) to give 3.3 g of Compound 27 as oily product in 91.3% yield.

NMR: $\delta^{CDCl_3}$ 4.52(d, J=6 Hz, 2H), 9.33(brs, 1H).

(2) To a solution of 3.3 g of Compound 27 in 100 ml of anhydrous benzene is added 0.8 ml of chloroacetyl chloride, and the mixture is refluxed for 2 hours and evaporated under reduced pressure. The residue (4.3 g) is purified on column chromatography (silica gel/methylene chloride) to give 1.9 g of Compound 28.

IR: $\nu_{max}^{film}$ 1695, 1690, 1685, 1590, 1560 cm$^{-1}$.

NMR: $\delta^{CDCl_3}$ 3.88 (AB, J=12 Hz, 2H), 4.72 (AB, J=14 Hz, 2H).

(3) A solution of 741 mg (1.7 mmoles) of Compound 28 and 338 mg (2 mmoles) of potassium iodide in 15 ml of dimethylformamide is stirred at 90° C. for 1 hour and cooled to −10° C. A solution of 40 mg (1.7 mmoles) of metallic sodium in 8 ml of ethanol is dropwise added thereto. The mixture is stirred at −10° C. for 30 minutes, poured into 300 ml of water, and extracted with ethyl acetate. The extract is washed with water, dried and evaporated under reduced pressure. The residue (742 mg) is purified on column chromatography (silica gel/methylene chloride) to give 398 mg of Compound 29 in 54% yield.

m.p. 118°-120° C.

IR: $\nu_{max}^{CHCl_3}$ 1668, 1590, 1565 cm$^{-1}$.

NMR: $\delta^{CDCl_3}$ 1.07 (t, J=8 Hz, 3H), 4.93(AB, J=16 Hz, 2H), 4.25(s,2H).

$^{13}$C-NMR: $\delta^{CDCl_3}$ 168.8, 103.2.

Elemental Analysis (for $C_{24}H_{22}O_3NCl_2$): Calcd(%): C, 65.02; H, 5.00; N, 3.16; Cl, 16.00. Found(%):C, 64.97; H, 4.72; N, 3.18; Cl, 16.20.

EXAMPLE 9

Preparation of 2-(N,N-dimethylcarbamoyl)-6-ethoxy-6-(2-chlorophenyl)-8-chloro-4H,6H-(1,2,4)triazolo[2,3-a][4,1]benzoxazepine

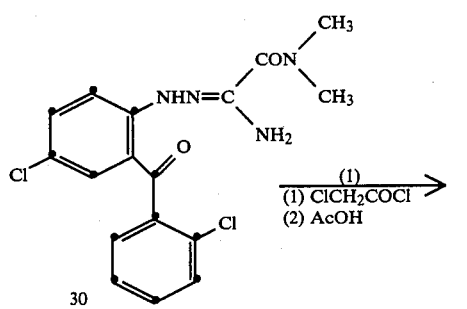

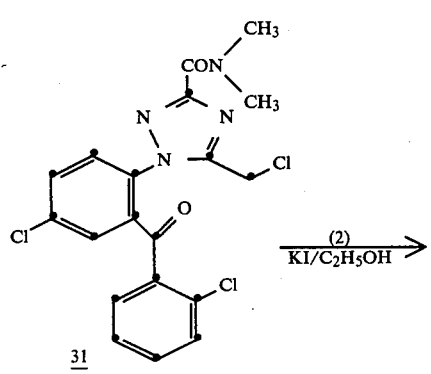

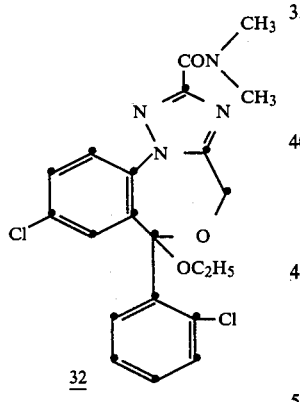

(1) To a suspension of 5.7 g of Compound 30 in 90 ml of benzene is added 2.55 g of chloroacetyl chloride, and the mixture is stirred for 30 minutes. A suspension of 3 g of potassium carbonate in 9 ml of dimethylformamide is added thereto, and the mixture is stirred for 4.5 hours, allowed to stand overnight, and evaporated under reduced pressure. The residue is neutralized with sodium hydrogencarbonate, and extracted with ethyl acetate. The extract is washed with water, dried, and evaporated. The residue is mixed with 45 ml of acetic acid, refluxed for 1.5 hours, and evaporated. The residue is neutralized with sodium hydrogencarbonate and extracted with chloroform. The extract is washed with water, dried and evaporated. The residue is crystallized from ether to give 6 g of Compound 31 in 91.2% yield, which is recrystallized from ethanol.

mp. 164°–165° C.

NMR: $\delta^{CDCl_3}$ 3.07, 4.58.

(2) Compound 31 (1.35 g) and potassium iodide (0.77 g) are suspended in 40 ml of ethanol, and the resulting suspension is refluxed for 30 minutes. A solution of 0.106 g of sodium in 10 ml of ethanol is added thereto, and the mixture is stirred for 4.5 hours and evaporated under reduced pressure. The residue is extracted with ether. The extract is washed with water, dried, and evaporated to give 0.8 g of Compound 32 in 58% yield, which is recrystallized from ethyl acetate.

mp. 156°–160° C.

NMR: $\delta^{CDCl_3}$ 1.12(t, J=7 Hz), 3.17, 3.30, 5.13+4.93(ABq, J=14 Hz)

Elemental Analysis (for $C_{21}H_{20}N_4Cl_2O_3$): Calcd(%):C, 56.39; H, 4.51; N, 12.53; Cl, 15.85. Found(%): C, 56.50; H, 4.48; N, 12.56; Cl, 15.95.

EXAMPLE 10

Preparation of 2-(N,N-dimethylcarbamoyl)-6-(2-chlorophenyl)-8-chloro-4H,6H-(1,2,4)triazolo[2,3-a][4,1]benzoxazepine

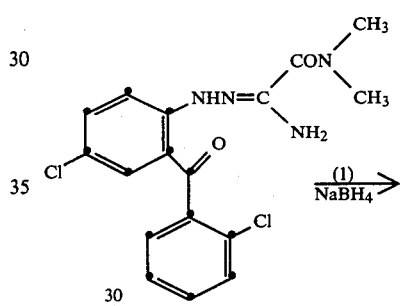

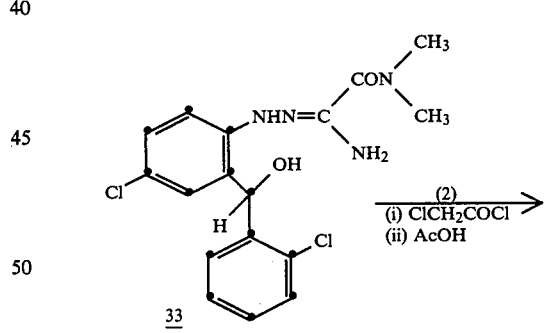

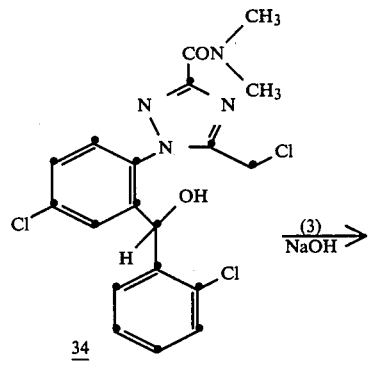

-continued

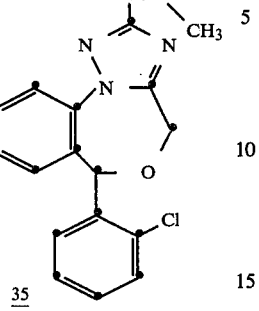

35

(1) To a solution of 3.8 g of Compound 30 in 75 ml of tetrahydrofuran is added a solution of 0.38 g of sodium borohydride in 6 ml of water, and the mixture is stirred for 30 minutes, mixed with water, neutralized with 10% hydrochloric acid and evaporated under reduced pressure. The residue is extracted with chloroform. The extract is washed with water and evaporated under reduced pressure. The residue is crystallized from ether to give 3.55 g of Compound 33 in 92.9% yield, which is recrystallized from ethyl acetate.

mp. 157°–159° C.

NMR: $\delta^{d_6\text{-}DMSO}$ 3.38, 3.02, 5.90 (d, J=6 Hz), 6.16(d, J=6 Hz), 7.73.

(2) Compound 33 (2.67 g) is treated in the same manner as Example 9 (1) to give 0.5 g of Compound 34 in 16.2% yield, which is crystallized from ethyl acetate.

mp. 166°–169° C.

Elemental Analysis (for $C_{19}H_{17}N_4Cl_3O_2$): Calcd(%): C, 51.90; H, 3.90; N, 12.74; Cl, 24.19. Found(%): C, 51.95; H, 3,82; N, 12.71; Cl, 23.95.

(3) To a solution of 1.4 g of Compound 34 in 140 ml of methanol is added 6 ml of 10% aqueous sodium hydroxide solution, and the mixture is stirred for 2 hours, neutralized with 10% hydrochloric acid and evaporated. The residue is extracted with ethyl acetate and the extract is washed with water, dried and evaporated. The residue is crystallized from ether to give 1.1 g of Compound 35 in 84.6% yield, which is recrystallized from ethyl acetate.

mp. 96°–98° C.

NMR: $\delta^{CDCl_3}$ 3.18, 3.33, 5.42+5.10(ABq, J=16 Hz), 5.93.

Elemental Analysis (for $C_{19}H_{16}N_4Cl_2O_2 \cdot \frac{1}{2}CH_3COOC_2H_5$): Calcd(%): C, 56.39; H, 4.51; N, 12.53; Cl, 15.85. Found(%): C, 56.43; H, 4.35; N, 12.90; Cl, 15.98.

(Alternative method)

-continued
(Alternative method)

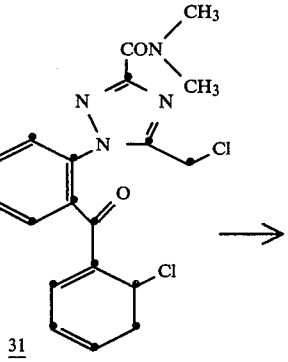

31

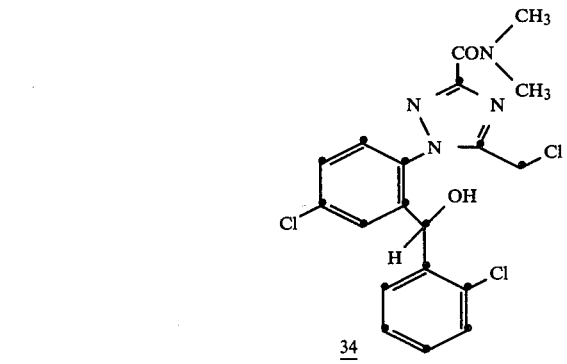

34

Compound 31 (1.1 g) and sodium borohydride (0.095 g) are dissolved in a mixture of 35 ml of tetrahydrofuran and 4 ml of water, and the resulting solution is stirred for 20 minutes, mixed with water, neutralized with 10% hydrochloric acid and evaporated under reduced pressure. The residue is extracted with ethyl acetate, washed with water, dried and evaporated to give 0.9 g of Compound 34 in 81.8% yield.

NMR: $\delta^{CDCl_3}$ 3.10, 3.25, 4.38+4.17 (ABq, J=13 Hz), 5.90 (d, J=5 Hz).

EXAMPLE 11

Preparation of 1-methyl-6-(2-chlorophenyl)-6-methoxy-8-chloro-4H,6H-(1,2,4)triazolo[4,3-a][4,1]benzoxazepine

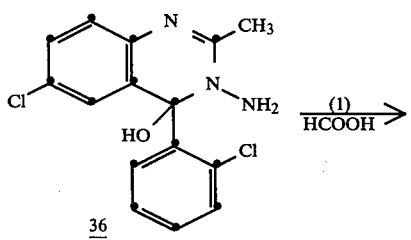

36

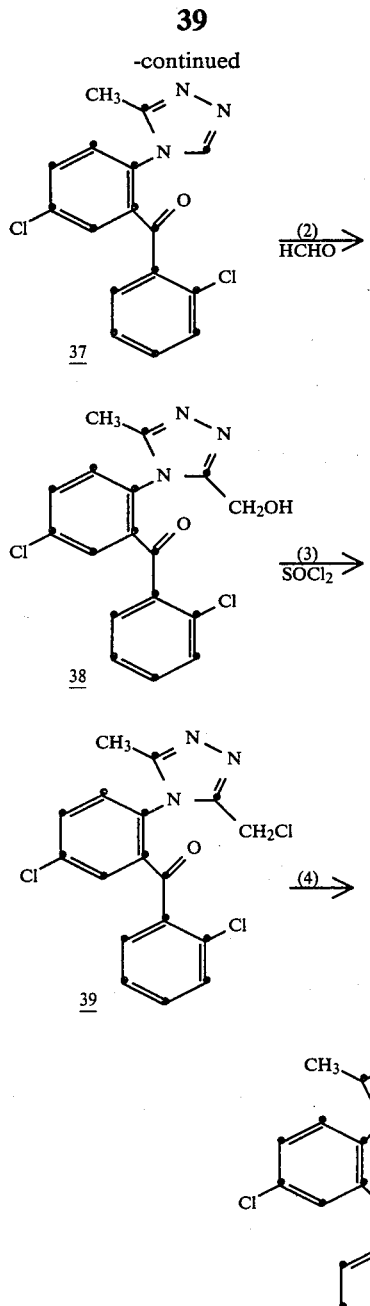

Elemental Analysis (for $C_{16}H_{11}ON_3Cl_2$): Calcd(%): C, 57.85; H, 3.34; N, 12.65; Cl, 21.35. Found(%): C, 57.72; H, 3.19; N, 12.67; Cl, 21.06.

(2) To a solution of 4.1 g of Compound 37 in 20 ml of xylene is added 5 g of paraformaldehyde at 125° C., and the mixture is stirred for 5 hours, and evaporated under reduced pressure. The residue is dissolved in chloroform and the insoluble materials are filtered off. The filtrate is evaporated under reduced pressure and the resulting residue is purified on chromatography (silica gel/ethyl acetate-methanol (30:5)) to give 3.3 g of Compound 38.

mp. 196.5°-197° C.

IR: $\nu_{max}^{Nujol}$ 3180, 1675, 1585 cm$^{-1}$.

NMR: $\delta^{CDCl_3}$ 2.17(s,3H), 4.42(ABq, J=14 Hz,2H).

Elemental Analysis (for $C_{17}H_{13}O_2N_3Cl_2$): Calcd(%): C, 56.37; H, 3.62; N, 11.62; Cl, 19.57. Found(%): C, 56.54; H, 3.59; N, 11.47; Cl, 19.65.

(3) A mixture of 3.3 g (9.1 mmoles) of Compound 38 and 5 ml of thionyl chloride is stirred at 60° C. for 1.5 hours, diluted with 150 ml of benzene, and evaporated under reduced pressure. This operation is repeated twice in order that the excess amount of reagent may be evaporated off. The resulting residue is mixed with 5% aqueous sodium hydrogencarbonate solution and ethyl acetate. The organic layer is washed with water, dried and evaporated. The residue (3.4 g) is purified on chromatography (silica gel/ethyl acetate-methanol (20:5)) to give 3.1 g of Compound 39 in 89.3% yield.

NMR: $\delta^{CDCl_3}$ 2.20 (s,3H), 4.47(ABq, J=13 Hz,2H).

(Alternative method)

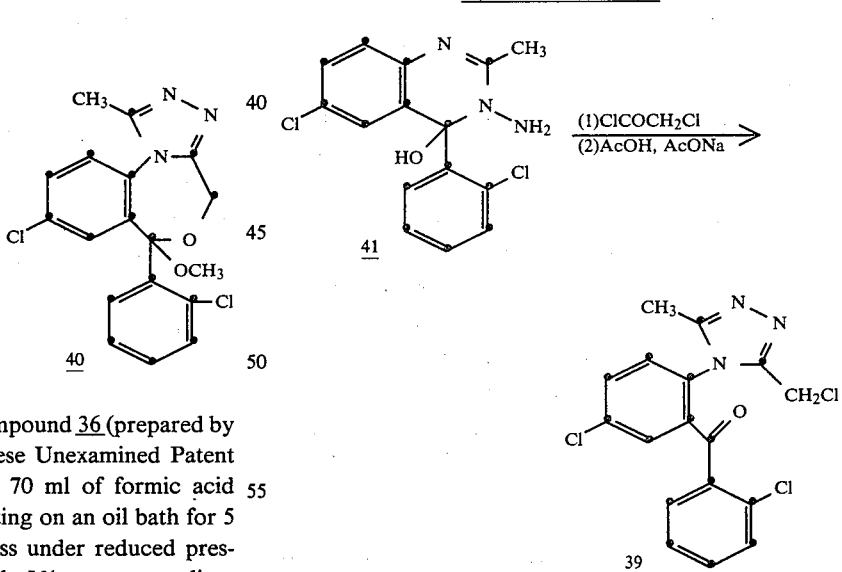

(1) The mixture of 15 g of Compound 36 (prepared by the method described in Japanese Unexamined Patent Publication No. 52-83469) and 70 ml of formic acid (78-80%) is refluxed under heating on an oil bath for 5 hours and evaporated to dryness under reduced pressure. The residue is mixed with 5% aqueous sodium hydrogencarbonate solution and chloroform and the organic layer is separated, washed with water, dried and evaporated under reduced pressure. The residue (17 g) is purified on column chromatography (silica gel/ethyl acetate-methanol (30:5)) to give 7.7 g of Compound 37.

mp. 154°-155° C.

IR: $\nu_{max}^{Nujol}$ 1680, 1580 cm$^{-1}$.

To a solution of 2.5 g of Compound 41 in 25 ml of dry dimethylformamide is added 1.8 ml of chloroacetylchloride at −5° C. with stirring, and the mixture is stirred at the same temperature for 2 hours and at room temperature for 4 hours. The precipitate (9.1 g), which is collected by filtration and washed with ether, is dissolved in 100 ml of glacial acetic acid. Sodium acetate (3.6 g) is added thereto, and the mixture is refluxed under heating on an oil bath for 1 hour and evaporated to dryness under reduced pressure. The residue is made alkaline with 5% aqueous sodium hydrogencarbonate solution and extracted with ethyl acetate. The organic layer is washed with water, dried, and evaporated. The resulting viscous residue is purified on chromatography (silica gel/ethyl acetate-methanol (20:3)) to give 5.9 g of Compound 39 in 60.9% yield.

(4) A solution of 1.5 g (3.9 mmoles) of Compound 39 and 981 mg of (5.9 mmoles) of potassium iodide in 40 ml of dry methanol is refluxed under heating on an oil bath for 30 minutes. A solution of 140 mg (6 mmoles) of metallic sodium in 30 ml of dry methanol is slowly dropwise added thereto, and the mixture is stirred for 5 hours and evaporated under reduced pressure. The residue is mixed with water and ethyl acetate, and the organic layer is separated, washed with water, dried, and evaporated. The residue (1.45 g) is treated on chromatography (silica gel/ethyl acetate-methanol (20:2)) to give 1.2 g of Compound 40 in 81% yield.

mp. 188°–189° C.

NMR: $\delta^{CDCl_3}$ 2.53 (s,3H), 2.97(s,3H), 4.68, 5.08 (AB, J=14 Hz,2H).

EXAMPLE 12

Preparation of 1-methyl-2-oxo-5-(2-chlorophenyl)-5-[2-(N,N-dimethylamino)ethoxy]-7-chloro-1,2,3,5-tetrahydro-[4,1]benzoxazepine

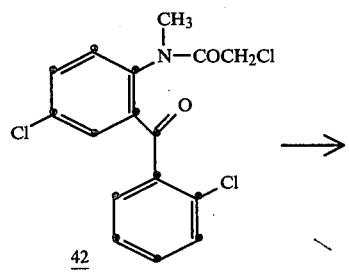 → 

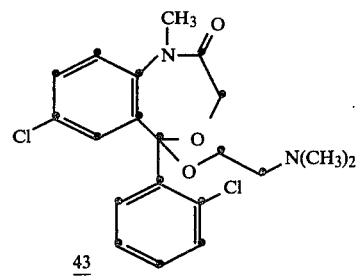

A suspension of 1.42 g of Compound 42 and 0.73 g of potassium iodide in 15 ml of acetone is refluxed for 1 hour and evaporated under reduced pressure. The residue is extracted with ethyl acetate, and the extract is washed with water, dried and evaporated. The residue is mixed with 2 ml of 2-(dimethylamino)ethanol, 50% suspension of 0.186 g of sodium hydride in mineral oil and 4 ml of dimethylformamide, and the mixture is stirred for 1 hour, diluted with water and extracted with ethyl acetate. The extract is dried and evaporated. The residue is purified on column chromatography (silica gel/methanol) to give 0.55 g of Compound 43 in 33.7% yield, which is recrystallized from ether.

mp. 130°–132° C.

Elemental Analysis (for $C_{20}H_{22}N_2Cl_2O_3$): Calcd(%): C, 58.69; H, 5.42; N, 6.84; Cl, 17.32. Found(%): C, 58.61; H, 5.45; N, 6.86; Cl, 17.32.

NMR: $\delta^{CDCl_3}$ 2.20, 3.17, 4.17.

EXAMPLE 13–21

The following compounds may be prepared in the same manners as mentioned above.

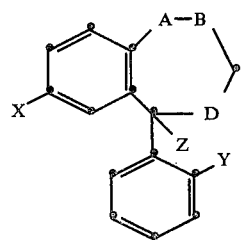

| Ex. No. | —A—B— | D | X | Y | Z | Yield (%) | mp. (°C.) | NMR:$\delta^{CDCl_3}$ | TLC |
|---|---|---|---|---|---|---|---|---|---|
| 13 | CH₃–C=N–N=CH (ring) | O | Cl | H | H | — | 227–229 | 2.47(s,3H), 4.63 + 4.97(AB,J = 13Hz,2H), 5.53(s,1H). | |
| 14 | " | " | " | F | " | 96 | 205–207 | 2.60(s,3H), 4.58 + 5.12(AB,J = 14Hz,2H), 5.70(s,1H). | |
| 15 | " | " | " | Cl | OC₂H₅ | — | 120–122 | 2.53(s,3H), 0.83(t, J = 7Hz,3H), 4.60 + 5.03(ABq,J = 13Hz,2H). | |
| 16 | " | " | " | " | OCH₂CH₂N(CH₃)₂ | 38.5 | 170– | 2.12, 2.52, 5.05 + | |

-continued

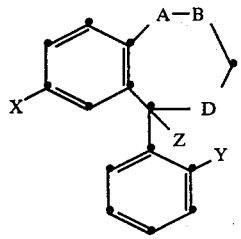

| Ex. No. | —A—B— | D | X | Y | Z | Yield (%) | mp. (°C.) | NMR:$\delta^{CDCl_3}$ | TLC |
|---|---|---|---|---|---|---|---|---|---|
| 17 | " | " | NO$_2$ | H | H | 83.3 | 173 215– 217 | 4.78(ABq,J = 13Hz). 2.20(s,3H), 4.85ABq (J = 13Hz,2H), 5.70(s, 1H). | IR:$\nu^{Nujol}$ 1620,1590, 1100,1090 (cm$^{-1}$) |
| 18 | 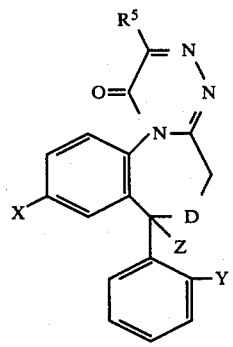 | " | " | " | " | — | 209– 212(d) | | IR:$\nu^{Nujol}$ 3100,1630, 1610,1280, 1250(cm$^{-1}$) |
| 19 | CH$_2$C$_6$H$_5$ \\ N—C \\ O | " | Cl | " | " | — | — | 2.18(s,6H), 4.23 (s,2H), 4.80(AB, J = 14Hz,2H). | |
| 20 | NH$_2$CH$_2$— triazole | " | " | " | OC$_2$H$_5$ | — | — | 1.75br, 5.07 + 4.80 (ABq) | |
| 21 | CH$_3$ triazine | S | " | " | H | 35.8 | 216– 219 | | Rf = 0.4 (silica gel/ ethyl acetate) |

We claim:

1. A compound of the formula:

[structure]

wherein
R$^5$ is C$_1$–C$_3$ alkyl,
D is oxygen or sulfur,
X is halogen or nitro,
Y is hydrogen or halogen, and
Z is hydrogen, C$_1$–C$_3$ alkoxy or C$_3$–C$_9$ dialkylaminoalkoxy; or a pharmaceutically acceptable salt thereof.

2. A compound according to claim 1, namely 1-oxo-2-methyl-7-(2-chlorophenyl)-9-chloro-1,12-dihydro-5H,7H-(1,2,4)triazino[4,3-a][4,1]benzoxazepine, or a pharmaceutically acceptable salt thereof.

3. A compound according to claim 1, namely 1-oxo-2-methyl-7-phenyl-9-chloro-1,12-dihydro-5H,7H-(1,2,4)triazino[4,3-a][4,1]benzothiazepine, or a pharmaceutically acceptable salt thereof.

* * * * *